United States Patent
Mirkov et al.

(10) Patent No.: US 10,285,333 B2
(45) Date of Patent: May 14, 2019

(54) PATHOGEN RESISTANT CITRUS COMPOSITIONS, ORGANISMS, SYSTEMS, AND METHODS

(71) Applicant: THE TEXAS A&M UNIVERSITY SYSTEM, College Station, TX (US)

(72) Inventors: T. Erik Mirkov, Harlingen, TX (US); Javier Gonzalez-Ramos, Brownsville, TX (US)

(73) Assignee: The Texas A&M University System, College Station, TX (US)

( * ) Notice: Subject to any disclaimer, the term of this patent is extended or adjusted under 35 U.S.C. 154(b) by 582 days.

(21) Appl. No.: 14/139,791

(22) Filed: Dec. 23, 2013

(65) Prior Publication Data

US 2014/0109472 A1     Apr. 24, 2014

Related U.S. Application Data

(63) Continuation of application No. 13/751,936, filed on Jan. 28, 2013.

(60) Provisional application No. 61/641,641, filed on May 2, 2012, provisional application No. 61/591,680, filed on Jan. 27, 2012.

(51) Int. Cl.
| | |
|---|---|
| *A01G 2/30* | (2018.01) |
| *C12N 15/82* | (2006.01) |
| *C07K 14/415* | (2006.01) |
| *A01N 65/00* | (2009.01) |
| *A01N 65/08* | (2009.01) |

(52) U.S. Cl.
CPC .............. *A01G 2/30* (2018.02); *A01N 65/00* (2013.01); *A01N 65/08* (2013.01); *C07K 14/415* (2013.01); *C12N 15/8279* (2013.01); *C12N 15/8281* (2013.01)

(58) Field of Classification Search
CPC ............ C12N 15/8281; C12N 15/8279; C12N 15/8205; C12N 15/8216; A01H 5/0806; A01G 1/06; A01G 2/30
See application file for complete search history.

(56) References Cited

U.S. PATENT DOCUMENTS

| | | | |
|---|---|---|---|
| 5,824,861 A | 10/1998 | Aldwinckle et al. | |
| 5,856,127 A | 1/1999 | Powell et al. | |
| 6,855,865 B2 | 2/2005 | Famodu et al. | |
| 7,001,739 B2 | 2/2006 | Mirkov et al. | |
| 7,141,427 B2 | 11/2006 | Mirkov et al. | |
| 7,238,781 B2 | 7/2007 | Famodu et al. | |
| 7,253,276 B2 | 8/2007 | Damaj et al. | |
| 7,323,622 B2 | 1/2008 | Mirkov et al. | |
| 7,534,614 B2 | 5/2009 | Mirkov et al. | |
| 7,632,936 B2 | 12/2009 | Mirkov et al. | |
| 7,632,937 B2 | 12/2009 | Mirkov et al. | |
| 7,754,946 B2 | 7/2010 | Damaj et al. | |
| 7,777,096 B2 | 8/2010 | Mirkov et al. | |
| 7,816,506 B2 | 10/2010 | Mirkov et al. | |
| 7,973,217 B2 | 7/2011 | Mirkov et al. | |
| 8,252,552 B2 | 8/2012 | Mirkov et al. | |
| 8,710,207 B2 | 4/2014 | Mirkov et al. | |
| 2002/0162141 A1 | 10/2002 | Mirkov et al. | |
| 2003/0099984 A1 | 5/2003 | Mirkov et al. | |
| 2004/0073965 A1 | 4/2004 | Mirkov et al. | |
| 2005/0005322 A1 | 1/2005 | Mirkov et al. | |
| 2005/0034192 A1 | 2/2005 | Damaj et al. | |
| 2005/0257285 A1 | 11/2005 | Gupta | |
| 2006/0269955 A1 | 11/2006 | Mirkov et al. | |
| 2006/0272047 A1 | 11/2006 | Mirkov et al. | |
| 2006/0272052 A1 | 11/2006 | Mirkov et al. | |
| 2007/0016979 A1 | 1/2007 | Damaj et al. | |
| 2007/0067880 A1 | 3/2007 | Mirkov et al. | |
| 2007/0130655 A1 | 6/2007 | Mirkov et al. | |
| 2008/0244794 A1 | 10/2008 | Mirkov et al. | |
| 2008/0271211 A1* | 10/2008 | Polston ................. | A01H 1/04 800/301 |
| 2010/0011460 A1 | 1/2010 | Damaj et al. | |
| 2010/0031396 A1 | 2/2010 | Mirkov et al. | |
| 2011/0283377 A1 | 11/2011 | Mirkov et al. | |
| 2012/0278946 A1 | 11/2012 | Mirkov et al. | |
| 2012/0311734 A1 | 12/2012 | Curtis et al. | |
| 2013/0071933 A1 | 3/2013 | Curtis | |
| 2013/0185826 A1 | 7/2013 | Mirkov et al. | |
| 2013/0205443 A1 | 8/2013 | Mirkov et al. | |
| 2013/0247252 A1 | 9/2013 | Damaj et al. | |
| 2014/0109472 A1 | 4/2014 | Mirkov et al. | |
| 2014/0208462 A1 | 7/2014 | Damaj et al. | |
| 2014/0283202 A1 | 9/2014 | Dickman et al. | |
| 2015/0259697 A1 | 9/2015 | Damaj et al. | |

FOREIGN PATENT DOCUMENTS

| | | |
|---|---|---|
| WO | 2004001012 A2 | 12/2003 |
| WO | 2007006079 A1 | 1/2007 |

OTHER PUBLICATIONS

Mirkov, T.E., 2010, "Genetic transformation of citrus with spinach defensins for broad spectrum resistance to bacteria and fungi", published online on May 17, 2010, retrieved from http://www.imok.ufl.edu/hlb/database/pdf/00001999.pdf.*

Grosser, Jude W., et al. 2009, "Grapefruit." Compendium of Transgenic Crop Plants 5:2:63-76.*

Mirkov, T.E., 2010, "Genetic transformation of citrus with spinach defensins for broad spectrum resistance to bacteria and fungi", published online on Dec. 17, 2009, retrieved online fromwww.imok.ufl.edu/hlb/database/pdf/00001999.pdf.*

(Continued)

*Primary Examiner* — Lee A Visone
*Assistant Examiner* — Weihua Fan
(74) *Attorney, Agent, or Firm* — Baker & McKenzie LLP

(57) ABSTRACT

The present disclosure relates, according to some embodiments, to pathogen resistant *citrus* compositions, organisms, systems, and methods. For example, a composition may comprise a peptide (e.g., a defensin peptide) and/or a nucleic acid (e.g., a defensin nucleic acid). A pathogen resistant *citrus* plant may comprise, in some embodiments, a defensin peptide and/or an expressable nucleic acid encoding a defensin peptide.

12 Claims, 16 Drawing Sheets

Specification includes a Sequence Listing.

(56) References Cited

OTHER PUBLICATIONS

Thomma, Bart P., Bruno P. Cammue, and Karin Thevissen. "Plant defensins." Planta 216.2 (2002): 193-202.*
Grosser, Jude W., et al. 2009, "Grapefruit." Compendium of Transgenic Crop Plants 5:2:63-76 (Year: 2009).*
Thomma, Bart P., Bruno P. Cammue, and Karin Thevissen. "Plant defensins." Planta 216.2 (2002): 193-202. (Year: 2002).*
Grosser, J. W., et al., "Grapefruit," Compendium of Transgenic Crop Plants: Transgenic Tropical and Subtropical Fruits and Nuts, Edited by C. Kole and T. C. Hall, Blackwell Publishing Ltd., (2008), 14 pages.
Dixon, D. C., et al., "Differential targeting of the tobacco PR-1 pathogenesis-related proteins to the extracellular space and vacuoles of crystal idioblasts," The EMBO Journal, vol. 10, No. 6, pp. 1317-1324, (1991), 8 pages.
Extended European Search Report, EP Appl. No. 13741390.2, dated Aug. 21, 2015, 5 pages.
Koziel, M. G., et al., "Optimizing expression of transgenes with an emphasis on post-transcriptional events," Plant Molecular Biology, vol. 32, pp. 393-405, (1996), 13 pages.
Dutt, M., et al., "Progress towards Incorporation of Antimicrobial Peptides for Disease Resistance in Citrus," Session 2, Biotechnology and Genomics, Proceedings of the International Society of Citriculture, 2008, pp. 259-264, China Agriculture Press, 2010, 7 pages.
Guerineau, F., et al., "Effect of two consensus sequences preceding the translation initiator codon on gene expression in plant protoplasts," Plant Molecular Biology, vol. 18, No. 4, pp. 815-818, (1992), 4 pages.
Segura, A., et al., "Novel defensin subfamily from spinach (*Spinacia oleracea*)," FEBS Letters, vol. 435, pp. 159-162, (1998), 4 pages.
U.S. Office Action, U.S. Appl. No. 13/751,936, dated Jul. 17, 2015, 18 pages.
Francis, M.I., et al., "Detached leaf inoculation of germplasm for rapid screening of resistance to citrus canker and citrus bacterial spot," Eur. J. Plant Pathol., (2010), vol. 127, pp. 571-578.
Irey, M.S., et al., "Comparison of Visual Assessment and Polymerase Chain Reaction Assay Testing to Estimate the Incidence of the Huanglongbing Pathogen in Commercial Florida Citrus," Proc. Fla. State Hort. Soc., (2006), vol. 119, pp. 89-93.
Larkin, M.A., et al., "Clustal W and Clustal X version 2.0," Bioinformatics Applications Note, vol. 23, No. 21, (2007), pp. 2947-2948.
Pearson, W.R., "Rapid Sequence Comparison: Rapid and Sensitive Sequence Comparison with FASTP and FASTA," Methods in Enzymology, vol. 183, (1990), 36 pages.
Pearson, W.R., et al., "Improved tools for biological sequence comparison," Proc. Natl. Acad. Sci., (1988), vol. 85, pp. 2444-2448.
Yang, Z.N., et al., "Agrobacterium-mediated transformation of the commercially important grapefruit cultivar Rio Red (*Citrus paradisi* Macf.)," Plant Cell Reports, (2000), vol. 19, pp. 1203-1211.
Kovalskaya, et al., "Antibacterial and Antifungal Activity of a Snakin-Defensin Hybrid Protein Expressed in Tobacco and Potato Plants," The Open Plant Science Journal, 2011, No. 5, pp. 29-42.
International Search Report and Written Opinion, PCT/US2013/023444, dated May 15, 2013, 11 pages.

Alvarez, S., et al., "Citrus Greening Disease (Huanglongbing) in Florida: Economic Impact, Management and the Potential for Biological Control," Agric Res, (Jun. 2016), vol. 5, No. 2, pp. 109-118.
Dewdney, M.M., et al., "2016 Florida Citrus Pest Management Guide: Ch. 27 Huanglongbing (Citrus Greening)," pp. 225, IFAS Extension, University of Florida, (2016), 3 pages.
Pagliai, F.A., et al., "The Transcriptional Activator LdtR from 'Candidatus Liberibacter asiaticus' Mediates Osmotic Stress Tolerance," PLOS Pathogens, (Apr. 2014), vol. 10, Issue 4, 19 pages.
Qureshi, J.A., et al., "Incidence of Invasive Diaphorina citri (Hemiptera: Psyllidae) and Its Introduced Parasitoid Tamarixia radiata (Hymenoptera: Eulophidae) in Florida Citrus," (2009), Journal of Economic Entomology, vol. 102, No. 1, pp. 247-256.
Mirkov, et al., U.S. Appl. No. 62/192,732, filed Jul. 15, 2015, 108 pages.
USDA: United States Department of Agriculture; Animal and Plant Health Inspection Service, "Citrus Greening: Citrus greening threatens America's citrus. Don't risk citrus, don't move citrus," Hungry Pests, www.hungrypests.com/the-threat/citrus-greening.php, (downloaded Aug. 8, 2016), 2 pages.
Semuels, A., The Atlantic, "Florida Without Oranges: A disease is decimating the citrus industry, leading some to wonder what's next for parts of the Sunshine State," (Jan. 27, 2015), 13 pages.
Gonsalves, A.K., et al., "Fusarium Primer," Crop Knowledge Master, www.extento.hawaii.edu/kbase/crop/type/fus_prim.htm, (downloaded Aug. 8, 2016), 8 pages.
Gottwald, T.R., et al., "Citrus canker," The Plant Health Instructor, www.apsnet.org/edcenter/intropp/lessons/prokaryotes/Pages/CitrusCanker.aspx, (2000), 10 pages.
Molina, A., et al., "Inhibition of bacterial and fungal plant pathogens by thionins of types I and II," Plant Science, (1998), pp. 169-177.
Schuster, A., et al., "Biology and biotechnology of Trichoderma," Appl Microbiol Biotechnol (2010), vol. 87, pp. 787-799.
Nijhuis, M., "The Green Death," The New Yorker, (Apr. 11, 2013), 3 pages.
Wang, N., et al., "Citrus Huanglongbing: A Newly Relevant Disease Presents Unprecedented Challenges," Phytopathology, (2013), vol. 103, No. 7, pp. 652-665.
Yadeta, K.A., et al., "The xylem as battleground for plant hosts and vascular wilt pathogens," Frontiers in Plant Science, Review Article, (Apr. 23, 2013), vol. 4, Article 97, 12 pages.
Parry, D., "Plant pathology in agriculture: Ch. 3 How does disease build up? Infection and colonisation by fungi"Cambridge University Press, (1990), pp. 57-59.
European Examination Report, EP Application No. 13741390.2, dated Sep. 20, 2016, 7 pages.
Bowman, K. et al., "Overview of Efforts to Develop HLB-Resistant Transgenic Citrus", Jan. 1, 2009, XP55221237, http://www.imok.ufl.edu/hlb/database/pdf/00001999.pdf, 67 pages.
European Examination Report dated Jul. 19, 2017 in connection with European Application No. 13741390.2, 4 pages.
Mexico Office Action dated Sep. 11, 2017 in connection with Mexican Application No. MX/a/2014/009113, 5 pages.
Chinese Fourth Office Action dated Jul. 31, 2017 in connection with Chinese Application No. 201380017222.8, 6 pages.

* cited by examiner

1-GIFSSRKCKTPSKTFKGICTRDSNCDT
SCRYEGYPAGDCKGIRRRCMCSKPC-52

1-GIFSSRKCKTPSKTFKGYCTRDSNCDT
SCRYEGYPAGD-38

GREENING INOCULATION TEST ON 'RIO RED' GRAPEFRUIT

NON-TRANSGENIC BUDS GRAFTED ON INFECTED ROOTSTOCK

SoD2 TRANSGENIC BUDS GRAFTED ON INFECTED ROOTSTOCK

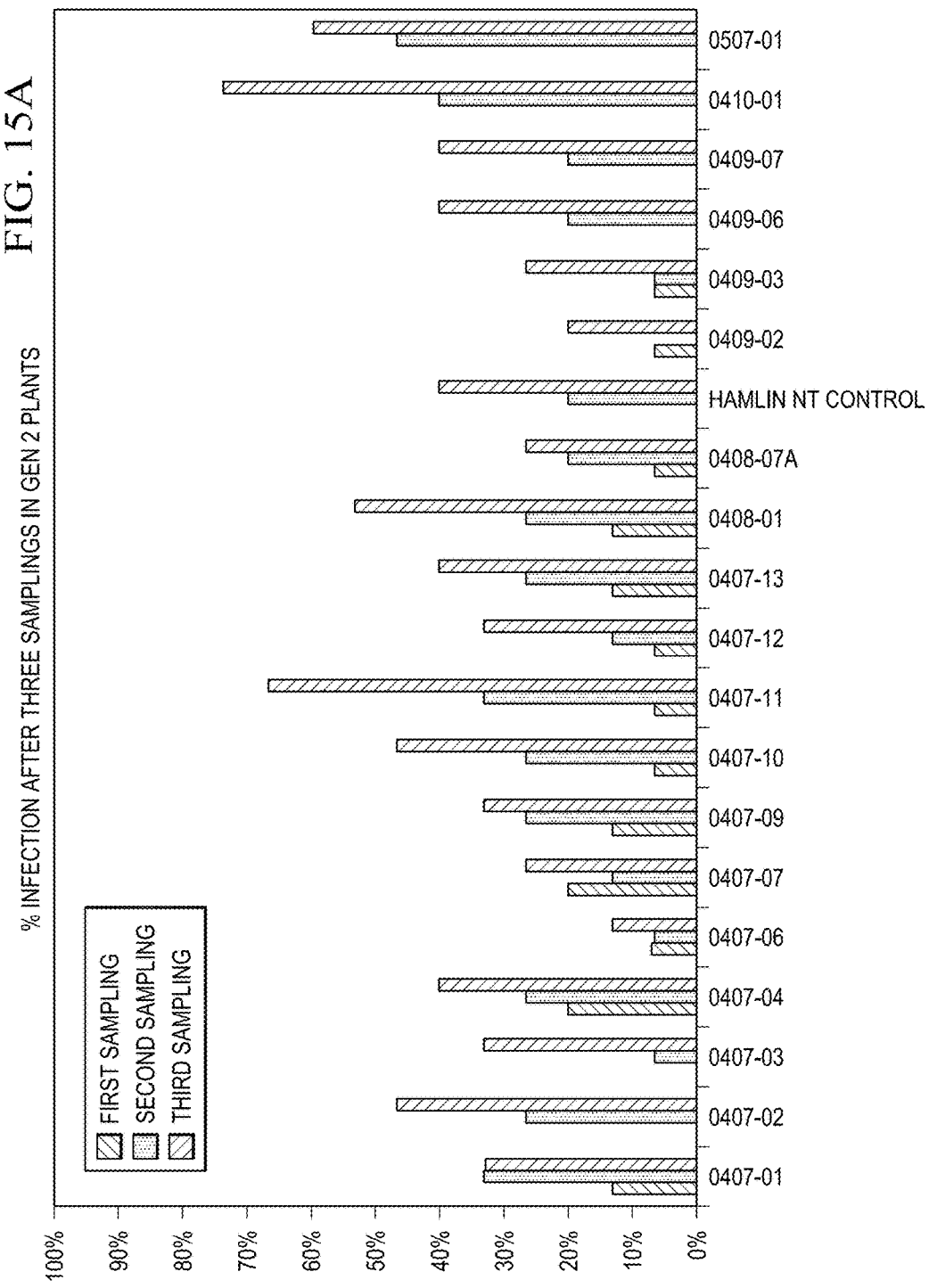

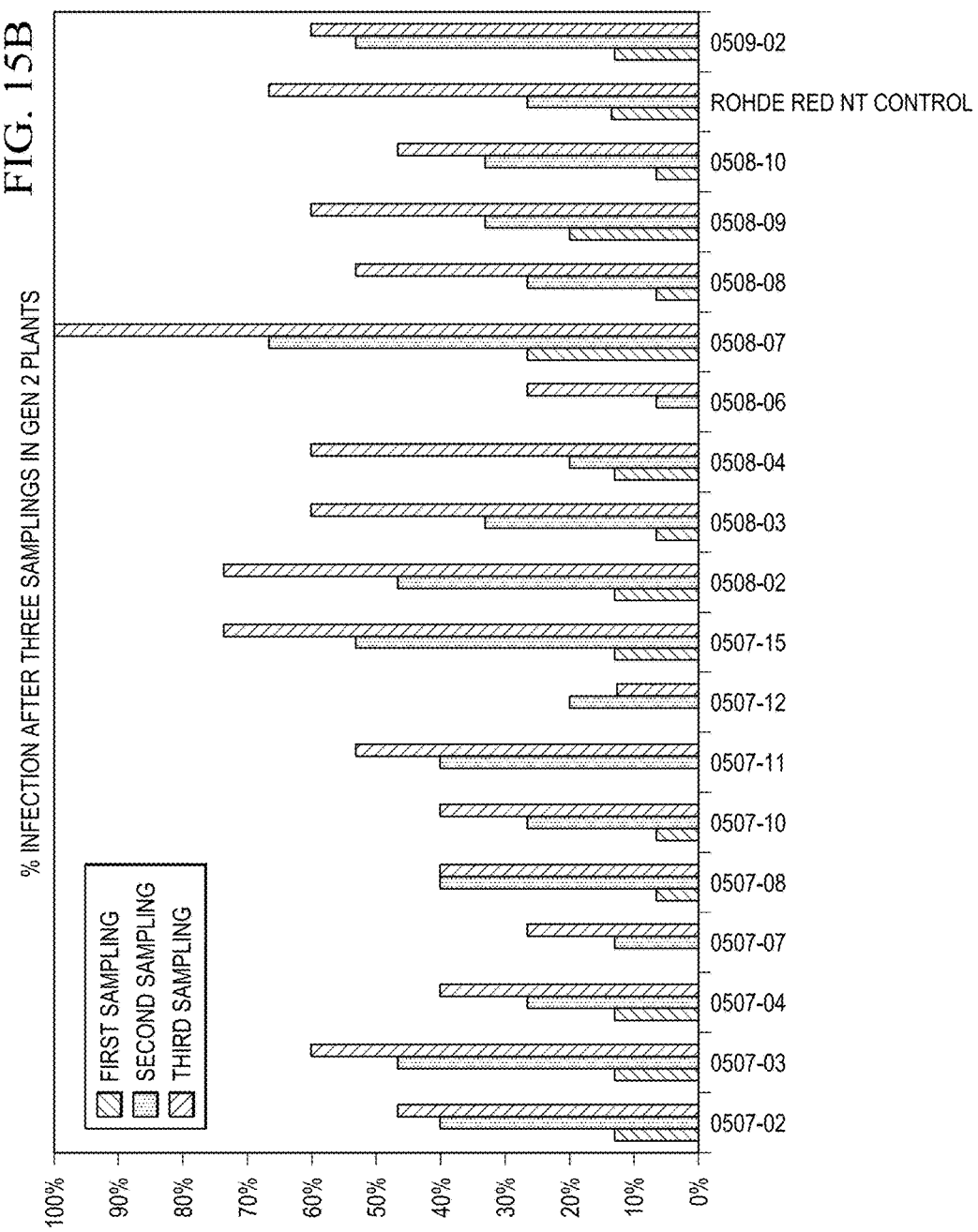

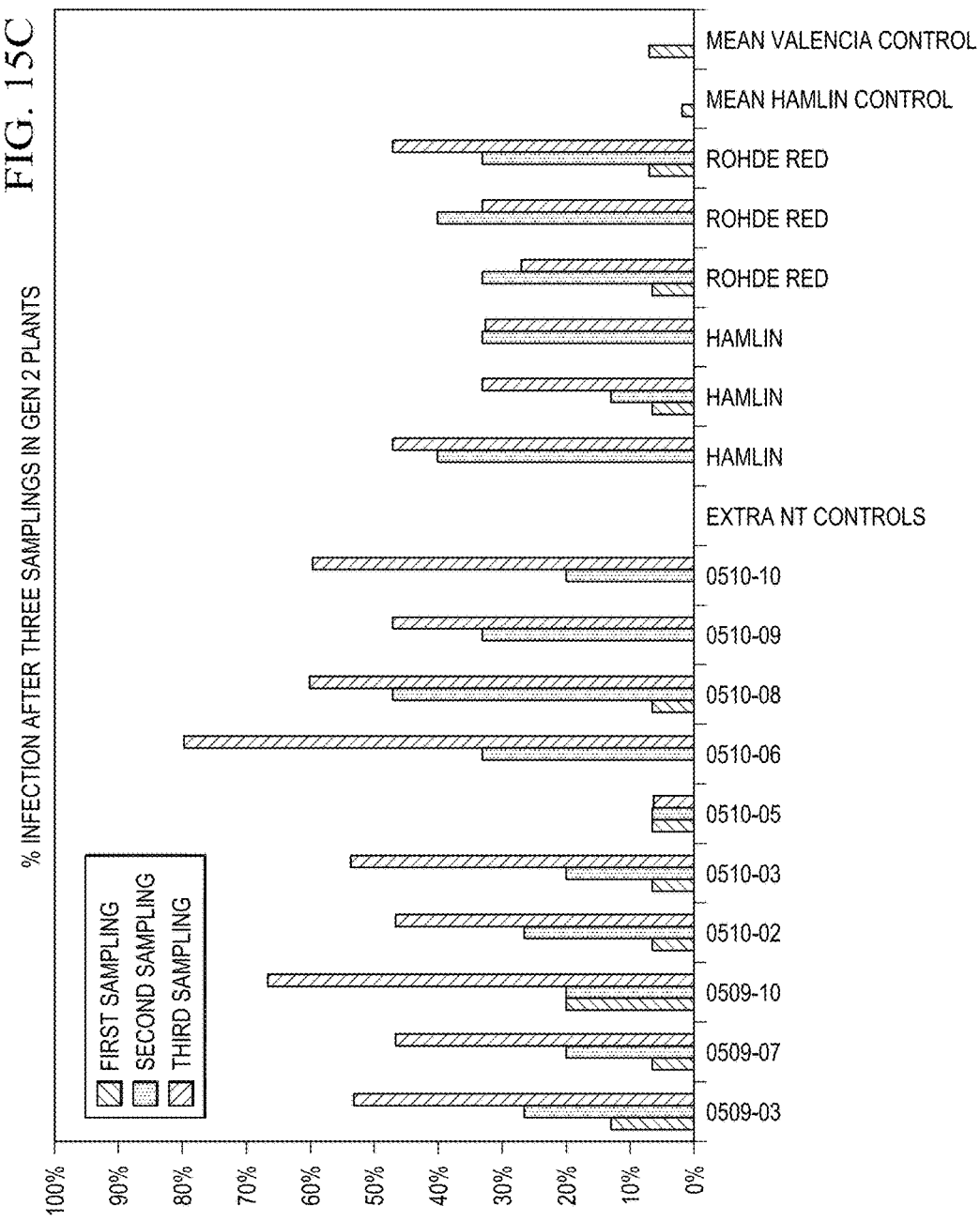

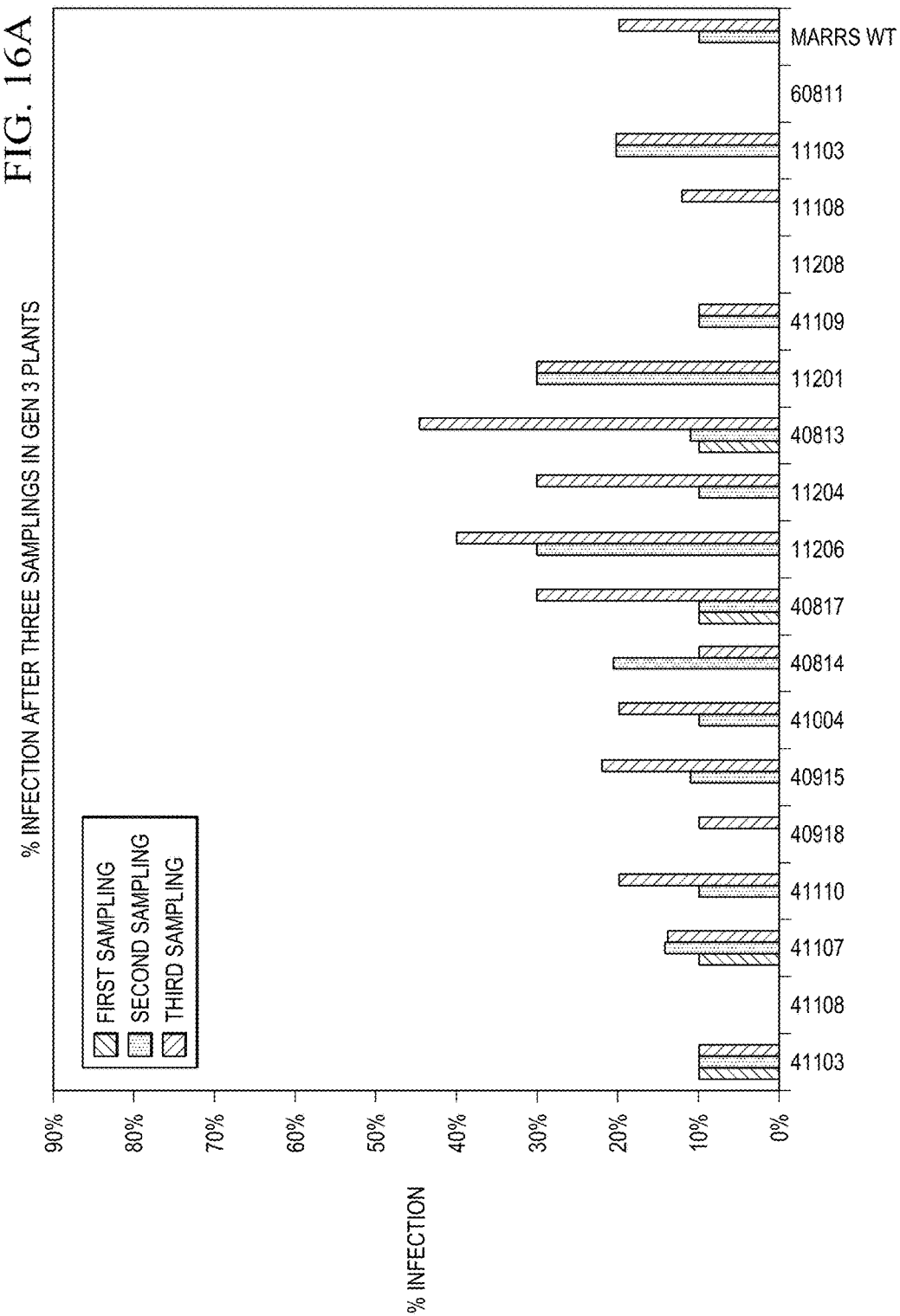

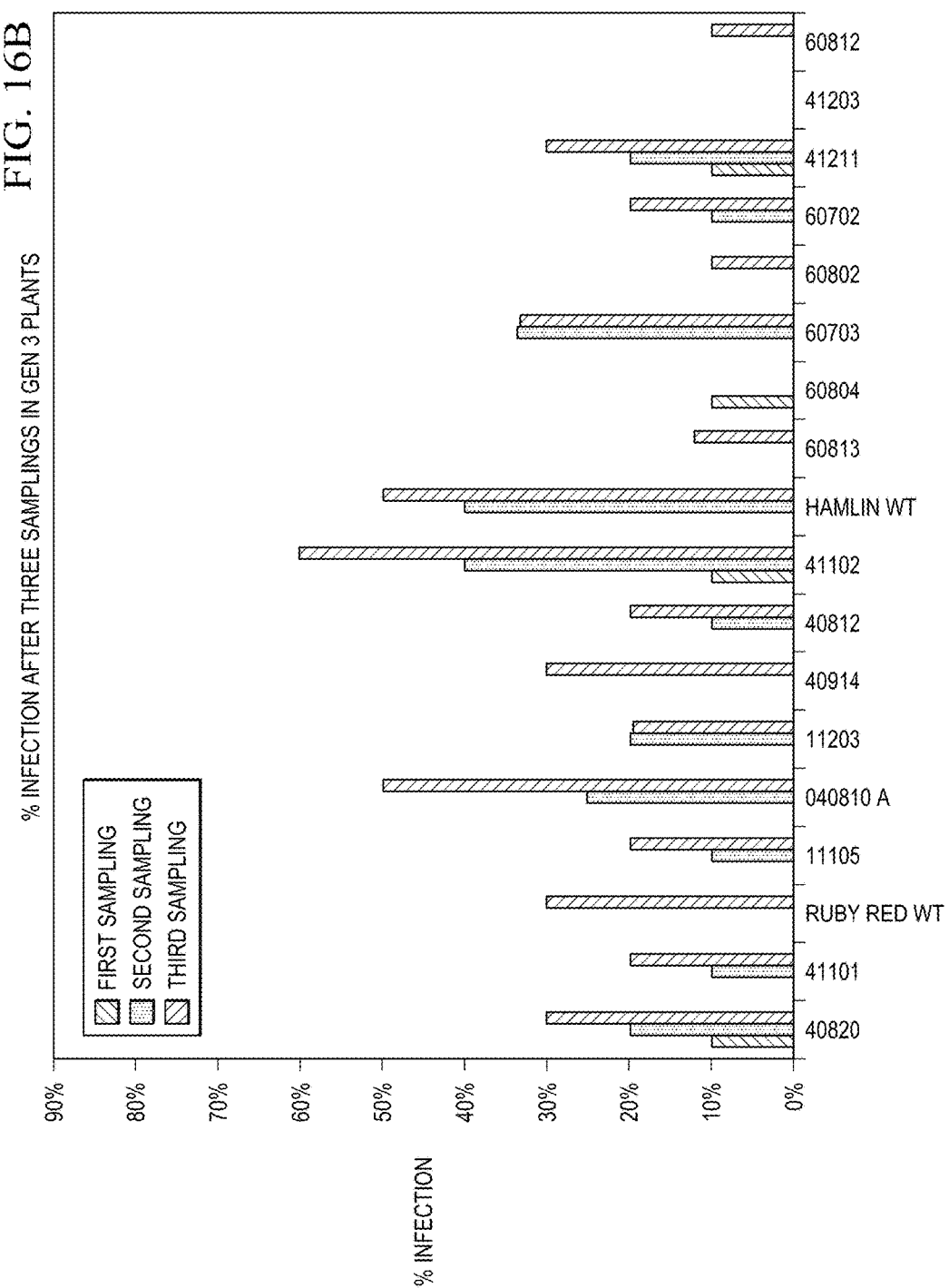

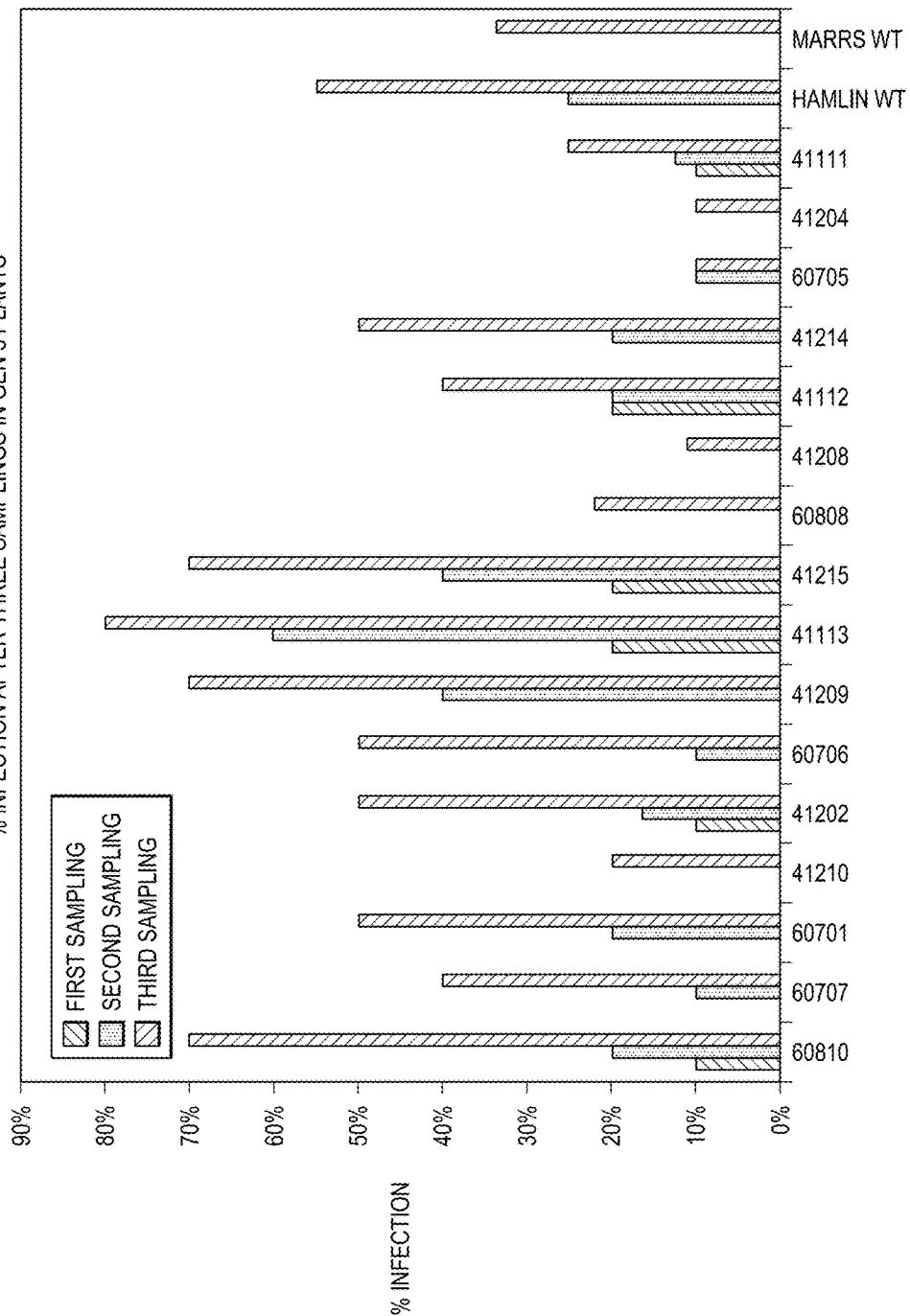

SEQUENCE LISTING

<160> NUMBER OF SEQ ID NOS: 31

<210> SEQ ID NO 1
<211> LENGTH: 52
<212> TYPE: PRT
<213> ORGANISM: Spinacia oleracea
<220> FEATURE:
<221> NAME/KEY: mat_peptide
<222> LOCATION: (1)..(52)
<223> OTHER INFORMATION: SoD2 peptide

<400> SEQUENCE: 1

Gly Ile Phe Ser Ser Arg Lys Cys Lys Thr Pro Ser Lys Thr Phe Lys
1               5                   10                  15

Gly Ile Cys Thr Arg Asp Ser Asn Cys Asp Thr Ser Cys Arg Tyr Glu
            20                  25                  30

Gly Tyr Pro Ala Gly Asp Cys Lys Gly Ile Arg Arg Cys Met Cys
        35                  40                  45

Ser Lys Pro Cys
    50

<210> SEQ ID NO 2
<211> LENGTH: 38
<212> TYPE: PRT
<213> ORGANISM: Spinacia oleracea
<220> FEATURE:
<221> NAME/KEY: mat_peptide
<222> LOCATION: (1)..(38)
<223> OTHER INFORMATION: SoD7 peptide

<400> SEQUENCE: 2

Gly Ile Phe Ser Ser Arg Lys Cys Lys Thr Pro Ser Lys Thr Phe Lys
1               5                   10                  15

Gly Tyr Cys Thr Arg Asp Ser Asn Cys Asp Thr Ser Cys Arg Tyr Glu
            20                  25                  30

Gly Tyr Pro Ala Gly Asp
        35

<210> SEQ ID NO 3
<211> LENGTH: 162
<212> TYPE: DNA
<213> ORGANISM: Artificial Sequence
<220> FEATURE:
<223> OTHER INFORMATION: SoD2 codon-optimized with GenScript

<400> SEQUENCE: 3
ggtattttct catctaggaa gtgcaaaact ccttcaaaga cttttaaggg aatttgcact       60
agggattcta attgcgatac ttcttgcaga tacgagggat atccagctgg cgattgcaaa      120
ggaattagga ggagatgtat gtgttcaaag ccatgttaat aa                         162

<210> SEQ ID NO 4
<211> LENGTH: 120
<212> TYPE: DNA
<213> ORGANISM: Artificial Sequence
<220> FEATURE:
<223> OTHER INFORMATION: SoD7 codon-optimized with GenScript

<400> SEQUENCE: 4
ggaattttct cttcaaggaa gtgcaagact ccatctaaga ctttcaaggg atattgtact       60
agggattcta actgcgatac atcatgcaga tacgagggct atcctgctgg cgattaataa      120

```
<210> SEQ ID NO 5
<211> LENGTH: 162
<212> TYPE: DNA
<213> ORGANISM: Artificial Sequence
<220> FEATURE:
<223> OTHER INFORMATION: SoD2 codon-optimized with CODA

<400> SEQUENCE: 5
ggtatctttt ctagtagaaa gtgtaagact ccttctaaga cttttaaagg tatttgcact      60
agagattcta attgtgacac ttcttgtaga tatgaaggtt atcctgctgg tgattgtaag     120
ggtattagaa gaagatgtat gtgttctaag ccttgttaat ag                       162

<210> SEQ ID NO 6
<211> LENGTH: 120
<212> TYPE: DNA
<213> ORGANISM: Artificial Sequence
<220> FEATURE:
<223> OTHER INFORMATION: SoD7 codon-optimized with CODA

<400> SEQUENCE: 6
ggtatttttt catctcgtaa gtgtaagact ccttctaaga cttttaaggg ttattgcact      60
agagattcta attgtgatac atcttgtaga tatgaaggtt atcctgctgg tgattaatag     120

<210> SEQ ID NO 7
<211> LENGTH: 82
<212> TYPE: PRT
<213> ORGANISM: Artificial Sequence
<220> FEATURE:
<223> OTHER INFORMATION: Chimeric peptide comprising a signal peptide
      and SoD2
<220> FEATURE:
<221> NAME/KEY: Signal
<222> LOCATION: (1)..(30)
<223> OTHER INFORMATION: PR-1b signal peptide
<220> FEATURE:
<221> NAME/KEY: mat_peptide
<222> LOCATION: (31)..(82)
<223> OTHER INFORMATION: SoD2 peptide

<400> SEQUENCE: 7

Met Gly Phe Phe Leu Phe Ser Gln Met Pro Ser Phe Phe Leu Val Ser
-30                 -25                 -20                 -15

Thr Leu Leu Leu Phe Leu Ile Ile Ser His Ser Ser His Ala Gly Ile
            -10                  -5                  -1   1

Phe Ser Ser Arg Lys Cys Lys Thr Pro Ser Lys Thr Phe Lys Gly Ile
                5                  10                  15

Cys Thr Arg Asp Ser Asn Cys Asp Thr Ser Cys Arg Tyr Glu Gly Tyr
            20                  25                  30

Pro Ala Gly Asp Cys Lys Gly Ile Arg Arg Arg Cys Met Cys Ser Lys
35                  40                  45                  50

Pro Cys

<210> SEQ ID NO 8
<211> LENGTH: 68
<212> TYPE: PRT
<213> ORGANISM: Artificial Sequence
<220> FEATURE:
<223> OTHER INFORMATION: Chimeric peptide comprising a signal peptide
      and SoD7
<220> FEATURE:
<221> NAME/KEY: Signal
<222> LOCATION: (1)..(30)
<223> OTHER INFORMATION: PR-1b signal peptide
<220> FEATURE:
<221> NAME/KEY: mat_peptide
```

-continued

```
<222> LOCATION: (31)..(68)
<223> OTHER INFORMATION: SoD7 peptide

<400> SEQUENCE: 8

Met Gly Phe Phe Leu Phe Ser Gln Met Pro Ser Phe Phe Leu Val Ser
-30                 -25                 -20                 -15

Thr Leu Leu Leu Phe Leu Ile Ile Ser His Ser Ser His Ala Gly Ile
                -10                  -5                  -1   1

Phe Ser Ser Arg Lys Cys Lys Thr Pro Ser Lys Thr Phe Lys Gly Tyr
         5                  10                  15

Cys Thr Arg Asp Ser Asn Cys Asp Thr Ser Cys Arg Tyr Glu Gly Tyr
     20                  25                  30

Pro Ala Gly Asp
35

<210> SEQ ID NO 9
<211> LENGTH: 268
<212> TYPE: DNA
<213> ORGANISM: Artificial Sequence
<220> FEATURE:
<223> OTHER INFORMATION: Chimeric nucleic acid encoding a signal peptide
      and SoD2 codon-optimized with GenScript
<220> FEATURE:
<221> NAME/KEY: misc_feature
<222> LOCATION: (1)..(6)
<223> OTHER INFORMATION: XbaI restriction site
<220> FEATURE:
<221> NAME/KEY: sig_peptide
<222> LOCATION: (11)..(100)
<223> OTHER INFORMATION: PR-1b signal peptide
<220> FEATURE:
<221> NAME/KEY: CDS
<222> LOCATION: (101)..(256)
<223> OTHER INFORMATION: GenScript-optimized SoD2 (07)
<220> FEATURE:
<221> NAME/KEY: misc_feture
<222> LOCATION: (263)..(268)
<223> OTHER INFORMATION: XbaI restriction site

<400> SEQUENCE: 9
tctagaaaca atgggcttct ccttttctc tcaaatgcct tcattttcc ttgtttctac      60 tcttcttctt tttcttatta tttctcattc ttctcatgct ggtatttct catctaggaa   120 gtgcaaaact ccttcaaaga cttttaaggg aatttgcact agggattcta attgcgatac   180
ttcttgcaga tacgagggat atccagctgg cgattgcaaa ggaattagga ggagatgtat   240
gtgttcaaag ccatgttaat aatctaga                                      268

<210> SEQ ID NO 10
<211> LENGTH: 226
<212> TYPE: DNA
<213> ORGANISM: Artificial Sequence
<220> FEATURE:
<223> OTHER INFORMATION: Chimeric nucleic acid encoding a signal peptide
      and SoD7 codon-optimized with GenScript
<220> FEATURE:
<221> NAME/KEY: misc_feature
<222> LOCATION: (1)..(6)
<223> OTHER INFORMATION: XbaI restriction site
<220> FEATURE:
<221> NAME/KEY: sig_peptide
<222> LOCATION: (11)..(100)
<223> OTHER INFORMATION: PR-1b signal peptide
<220> FEATURE:
<221> NAME/KEY: CDS
<222> LOCATION: (101)..(214)
<223> OTHER INFORMATION: GenScript-optimized SoD7 (08)
<220> FEATURE:
<221> NAME/KEY: misc_feature
```

<222> LOCATION: (221)..(226)
<223> OTHER INFORMATION: XbaI restriction site

<400> SEQUENCE: 10
tctagaaaca atgggtttct tcttgttttc tcaaatgcct tcattctttc ttgtttcaac      60
tttgcttctt tttcttatta tttctcattc atctcatgct ggaattttct cttcaaggaa     120
gtgcaagact ccatctaaga ctttcaaggg atattgtact agggattcta actgcgatac     180
atcatgcaga tacgagggct atcctgctgg cgattaataa tctaga                    226

<210> SEQ ID NO 11
<211> LENGTH: 268
<212> TYPE: DNA
<213> ORGANISM: Artificial Sequence
<220> FEATURE:
<223> OTHER INFORMATION: Chimeric nucleic acid encoding a signal peptide
      and SoD2 codon-optimized with CODA
<220> FEATURE:
<221> NAME/KEY: misc-feature
<222> LOCATION: (1)..(6)
<223> OTHER INFORMATION: XbaI restriction site
<220> FEATURE:
<221> NAME/KEY: sig_peptide
<222> LOCATION: (11)..(100)
<223> OTHER INFORMATION: PR-1b signal peptide
<220> FEATURE:
<221> NAME/KEY: CDS
<222> LOCATION: (101)..(256)
<223> OTHER INFORMATION: CODA-optimized SoD2 (09)
<220> FEATURE:
<221> NAME/KEY: misc_feature
<222> LOCATION: (263)..(268)
<223> OTHER INFORMATION: Sac I, SstI restriction site

<400> SEQUENCE: 11
tctagaaaca atgggtttct ttttgttttc tcaaatgcct tcattttcc ttgtgtctac       60 tcttcttctt tttcttatta tttctcattc ttctcatgct ggtatctttt ctagtagaaa     120
gtgtaagact ccttctaaga cttttaaagg tatttgcact agagattcta attgtgacac     180
ttcttgtaga tatgaaggtt atcctgctgg tgattgtaag ggtattagaa gaagatgtat     240
gtgttctaag ccttgttaat aggagctc                                        268

<210> SEQ ID NO 12
<211> LENGTH: 226
<212> TYPE: DNA
<213> ORGANISM: Artificial Sequence
<220> FEATURE:
<223> OTHER INFORMATION: Chimeric nucleic acid encoding a signal peptide
      and SoD7 codon-optimized with CODA
<220> FEATURE:
<221> NAME/KEY: misc_feature
<222> LOCATION: (1)..(6)
<223> OTHER INFORMATION: XbaI restriction site
<220> FEATURE:
<221> NAME/KEY: sig_peptide
<222> LOCATION: (11)..(100)
<223> OTHER INFORMATION: PR-1b signal peptide
<220> FEATURE:
<221> NAME/KEY: CDS
<222> LOCATION: (101)..(214)
<223> OTHER INFORMATION: CODA-optimized SoD7 (10)
<220> FEATURE:
<221> NAME/KEY: misc_feature
<222> LOCATION: (221)..(226)
<223> OTHER INFORMATION: SacI, SstI restriction site

<400> SEQUENCE: 12
tctagaaaca atgggattct ttttgttttc tcaaatgcct tctttctttc ttgtgtctac      60

```
tcttcttctt tttcttatta tttctcattc ttctcatgct ggtattttt catctcgtaa    120 gtgtaagact ccttctaaga cttttaaggg ttattgcact agagattcta attgtgatac    180
atcttgtaga tatgaaggtt atcctgctgg tgattaatag gagctc                    226
```

<210> SEQ ID NO 13
<211> LENGTH: 1462
<212> TYPE: DNA
<213> ORGANISM: Artificial Sequence
<220> FEATURE:
<223> OTHER INFORMATION: SoD2 expression cassette comprising a chimeric
      nucleic acid encoding a signal peptide and SoD2
<220> FEATURE:
<221> NAME/KEY: promoter
<222> LOCATION: (1)..(780)
<223> OTHER INFORMATION: 35SP
<220> FEATURE:
<221> NAME/KEY: 5'UTR
<222> LOCATION: (781)..(923)
<223> OTHER INFORMATION: TEV 5' UTR
<220> FEATURE:
<221> NAME/KEY: misc_feature
<222> LOCATION: (924)..(929)
<223> OTHER INFORMATION: XbaI restriction site
<220> FEATURE:
<221> NAME/KEY: sig_peptide
<222> LOCATION: (934)..(1023)
<223> OTHER INFORMATION: PR-1b signal peptide
<220> FEATURE:
<221> NAME/KEY: CDS
<222> LOCATION: (1024)..(1179)
<223> OTHER INFORMATION: encodes SoD2 peptide
<220> FEATURE:
<221> NAME/KEY: misc_feature
<222> LOCATION: (1186)..(1191)
<223> OTHER INFORMATION: SacI, SstI restriction site
<220> FEATURE:
<221> NAME/KEY: misc_feature
<222> LOCATION: (1192)..(1257)
<223> OTHER INFORMATION: polylinker
<220> FEATURE:
<221> NAME/KEY: terminator
<222> LOCATION: (1257)..(1462)
<223> OTHER INFORMATION: 35ST

<400> SEQUENCE: 13

```
atggtggagc acgacactct cgtctactcc aagaatatca agatacagt ctcagaagac     60 caaagggcta ttgagacttt tcaacaaagg gtaatatcgg gaaacctcct cggattccat    120
tgcccagcta tctgtcactt catcaaaagg acagtagaaa aggaaggtgg cacctacaaa    180
tgccatcatt gcgataaagg aaaggctatc gttcaagatg cctctgccga cagtggtccc    240
aaagatggac cccacccac gaggagcatc gtggaaaaag aagacgttcc aaccacgtct     300
tcaaagcaag tggattgatg tgataacatg gtggagcacg acactctcgt ctactccaag    360
aatatcaaag atacagtctc agaagaccaa agggctattg agactttca acaagggta      420 atatcgggaa acctcctcgg attccattgc ccagctatct gtcacttcat caaaaggaca    480
gtagaaaagg aaggtggcac ctacaaatgc catcattgcg ataaaggaaa ggctatcgtt    540
caagatgcct ctgccgacag tggtcccaaa gatggacccc acccacgag gagcatcgtg     600 gaaaagaag acgttccaac cacgtcttca aagcaagtgg attgatgtga tatctccact    660
gacgtaaggg atgacgcaca atcccactat ccttcgcaag accttcctct atataaggaa    720
gttcatttca tttggagagg acacgctgaa atcaccagtc tctctctaca atctatctc     780 aaataacaaa tctcaacaca acatatacaa acaaacgaa tctcaagcaa tcaagcattc     840
tacttctatt gcagcaattt aaatcatttc ttttaaagca aaagcaattt tctgaaaatt    900
```

```
ttcaccatttt acgaacgata gcatctagaa acaatgggct tcttcctttt ctctcaaatg    960
ccttcatttt tccttgtttc tactcttctt cttttttctta ttatttctca ttcttctcat   1020
gctggtattt tctcatctag gaagtgcaaa actccttcaa agactttaa gggaatttgc     1080 actagggatt ctaattgcga tacttcttgc agatacgagg gatatccagc tggcgattgc    1140
aaaggaatta ggaggagatg tatgtgttca agccatgtt aataatctag aacgcgtgaa    1200
ttcgaggcct cggatccctc gaggagctcg gtacccgggg tccgcaaaaa tcaccagtct   1260
ctctctacaa atctatctct ctctattttt ctccagaata atgtgtgagt agttcccaga   1320
taagggaatt agggttctta tagggtttcg ctcatgtgtt gagcatataa gaaacccta    1380 gtatgtattt gtatttgtaa aatacttcta tcaataaaat ttctaattcc taaaaccaaa   1440
atccagtgac ctgcaggcat gc                                             1462

<210> SEQ ID NO 14
<211> LENGTH: 1420
<212> TYPE: DNA
<213> ORGANISM: Artificial Sequence
<220> FEATURE:
<223> OTHER INFORMATION: SoD7 expression cassette comprising a chimeric
      nucleic acid encoding a signal peptide and SoD7
<220> FEATURE:
<221> NAME/KEY: promoter
<222> LOCATION: (1)..(780)
<223> OTHER INFORMATION: 35SP
<220> FEATURE:
<221> NAME/KEY: 5'UTR
<222> LOCATION: (781)..(923)
<223> OTHER INFORMATION: TEV 5' UTR
<220> FEATURE:
<221> NAME/KEY: misc_feature
<222> LOCATION: (924)..(929)
<223> OTHER INFORMATION: XbaI restriction site
<220> FEATURE:
<221> NAME/KEY: sig_peptide
<222> LOCATION: (934)..(1023)
<223> OTHER INFORMATION: PR-1b signal peptide
<220> FEATURE:
<221> NAME/KEY: CDS
<222> LOCATION: (1024)..(1143)
<223> OTHER INFORMATION: Encodes SoD7 peptide
<220> FEATURE:
<221> NAME/KEY: misc_feature
<222> LOCATION: (1144)..(1149)
<223> OTHER INFORMATION: SacI, SstI restriction site
<220> FEATURE:
<221> NAME/KEY: misc_feature
<222> LOCATION: (1150)..(1215)
<223> OTHER INFORMATION: polylinker
<220> FEATURE:
<221> NAME/KEY: terminator
<222> LOCATION: (1216)..(1420)
<223> OTHER INFORMATION: 35ST

<400> SEQUENCE: 14
atggtggagc acgacactct cgtctactcc aagaatatca agatacagt ctcagaagac      60 caaagggcta ttgagacttt tcaacaaagg gtaatatcgg gaaacctcct cggattccat    120
tgcccagcta tctgtcactt catcaaaagg acagtagaaa aggaaggtgg cacctacaaa   180
tgccatcatt gcgataaagg aaaggctatc gttcaagatg cctctgccga cagtggtccc   240
aaagatggac cccacccac gaggagcatc gtggaaaag aagacgttcc aaccacgtct    300
tcaaagcaag tggattgatg tgataacatg gtggagcacg acactctcgt ctactccaag   360
aatatcaaag atacagtctc agaagaccaa agggctattg agacttttca acaaagggta   420
atatcgggaa acctcctcgg attccattgc ccagctatct gtcacttcat caaaggaca    480
```

```
gtagaaaagg aaggtggcac ctacaaatgc catcattgcg ataaaggaaa ggctatcgtt    540
caagatgcct ctgccgacag tggtcccaaa gatggacccc cacccacgag gagcatcgtg    600 gaaaagaag acgttccaac cacgtcttca aagcaagtgg attgatgtga tatctccact    660
gacgtaaggg atgacgcaca atcccactat ccttcgcaag accttcctct atataaggaa    720
gttcatttca tttggagagg acacgctgaa atcaccagtc tctctctaca aatctatctc    780
aaataacaaa tctcaacaca acatatacaa aacaaacgaa tctcaagcaa tcaagcattc    840
tacttctatt gcagcaattt aaatcatttc ttttaaagca aaagcaattt tctgaaaatt    900
ttcaccattt acgaacgata gcatctagaa acaatgggtt tcttcttgtt ttctcaaatg    960
ccttcattct ttcttgtttc aactttgctt cttttttctta ttatttctca ttcatctcat   1020
gctggaattt tctcttcaag gaagtgcaag actccatcta agactttcaa gggatattgt   1080
actagggatt ctaactgcga tacatcatgc agatacgagg gctatcctgc tggcgattaa   1140
taatctagaa cgcgtgaatt cgaggcctcg gatccctcga ggagctcggt acccggggtc   1200
cgcaaaaatc accagtctct ctctacaaat ctatctctct ctattttctct ccagaataat   1260 gtgtgagtag ttcccagata agggaattag ggttcttata gggtttcgct catgtgttga   1320
gcatataaga aacccttagt atgtatttgt atttgtaaaa tacttctatc aataaaattt   1380
ctaattccta aaaccaaaat ccagtgacct gcaggcatgc                          1420
```

<210> SEQ ID NO 15
<211> LENGTH: 1424
<212> TYPE: DNA
<213> ORGANISM: Artificial Sequence
<220> FEATURE:
<223> OTHER INFORMATION: Chimeric nucleic acid encoding a signal peptide
      and SoD2
<220> FEATURE:
<221> NAME/KEY: promoter
<222> LOCATION: (1)..(780)
<223> OTHER INFORMATION: 35SP
<220> FEATURE:
<221> NAME/KEY: 5'UTR
<222> LOCATION: (781)..(923)
<223> OTHER INFORMATION: TEV 5' UTR
<220> FEATURE:
<221> NAME/KEY: misc_feature
<222> LOCATION: (924)..(929)
<223> OTHER INFORMATION: XbaI restriction site
<220> FEATURE:
<221> NAME/KEY: sig_peptide
<222> LOCATION: (934)..(1023)
<223> OTHER INFORMATION: PR-1b signal peptide
<220> FEATURE:
<221> NAME/KEY: CDS
<222> LOCATION: (1024)..(1179)
<223> OTHER INFORMATION: Encodes SoD7 peptide
<220> FEATURE:
<221> NAME/KEY: misc_feature
<222> LOCATION: (1186)..(1191)
<223> OTHER INFORMATION: SacI, SstI restriction site
<220> FEATURE:
<221> NAME/KEY: misc_feature
<222> LOCATION: (1192)..(1219)
<223> OTHER INFORMATION: polylinker
<220> FEATURE:
<221> NAME/KEY: terminator
<222> LOCATION: (1220)..(1424)
<223> OTHER INFORMATION: 35ST

<400> SEQUENCE: 15

```
atggtggagc acgacactct cgtctactcc aagaatatca agatacagt ctcagaagac     60 caaagggcta ttgagacttt tcaacaaagg gtaatatcgg gaaacctcct cggattccat   120
```

```
tgcccagcta tctgtcactt catcaaaagg acagtagaaa aggaaggtgg cacctacaaa      180
tgccatcatt gcgataaagg aaaggctatc gttcaagatg cctctgccga cagtggtccc      240
aaagatggac ccccacccac gaggagcatc gtggaaaaag aagacgttcc aaccacgtct      300
tcaaagcaag tggattgatg tgataacatg gtggagcacg acactctcgt ctactccaag      360
aatatcaaag atacagtctc agaagaccaa agggctattg agacttttca acaaagggta      420
atatcgggaa acctcctcgg attccattgc ccagctatct gtcacttcat caaaaggaca      480
gtagaaaagg aaggtggcac ctacaaatgc catcattgcg ataaaggaaa ggctatcgtt      540
caagatgcct ctgccgacag tggtcccaaa gatggacccc cacccacgag gagcatcgtg      600 gaaaagaag acgttccaac cacgtcttca aagcaagtgg attgatgtga tatctccact       660
gacgtaaggg atgacgcaca atcccactat ccttcgcaag accttcctct atataaggaa      720
gttcatttca tttggagagg acacgctgaa atcaccagtc tctctctaca aatctatctc      780
aaataacaaa tctcaacaca acatatacaa aacaaacgaa tctcaagcaa tcaagcattc      840
tacttctatt gcagcaattt aaatcatttc ttttaaagca aaagcaattt tctgaaaatt      900
ttcaccattt acgaacgata gcatctagaa acaatgggtt tcttttttgtt ttctcaaatg     960 ccttcatttt tccttgtgtc tactcttctt cttttttctta ttatttctca ttcttctcat    1020
gctggtatct tttctagtag aaagtgtaag actccttcta agacttttaa aggtatttgc     1080
actagagatt ctaattgtga cacttcttgt agatatgaag gttatcctgc tggtgattgt     1140
aagggtatta gaagaagatg tatgtgttct aagccttgtt aataggagct cggtacccgg     1200
ggtccgcaaa atcaccagt ctctctctac aaatctatct ctctctattt ttctccagaa      1260
taatgtgtga gtagttccca gataagggaa ttagggttct tatagggttt cgctcatgtg     1320
ttgagcatat aagaaaccct tagtatgtat ttgtatttgt aaaatacttc tatcaataaa     1380
atttctaatt cctaaaacca aaatccagtg acctgcaggc atgc                      1424
```

<210> SEQ ID NO 16
<211> LENGTH: 1388
<212> TYPE: DNA
<213> ORGANISM: Artificial Sequence
<220> FEATURE:
<223> OTHER INFORMATION: Chimeric nucleic acid encoding a signal peptide
      and SoD7
<220> FEATURE:
<221> NAME/KEY: promoter
<222> LOCATION: (1)..(780)
<223> OTHER INFORMATION: 35SP
<220> FEATURE:
<221> NAME/KEY: 5'UTR
<222> LOCATION: (781)..(923)
<223> OTHER INFORMATION: TEV 5' UTR
<220> FEATURE:
<221> NAME/KEY: misc_feature
<222> LOCATION: (781)..(923)
<223> OTHER INFORMATION: XbaI restriction site
<220> FEATURE:
<221> NAME/KEY: sig_peptide
<222> LOCATION: (934)..(1023)
<223> OTHER INFORMATION: PR-1b signal peptide
<220> FEATURE:
<221> NAME/KEY: CDS
<222> LOCATION: (1024)..(1137)
<223> OTHER INFORMATION: Encodes SoD7 peptide
<220> FEATURE:
<221> NAME/KEY: misc_feature
<222> LOCATION: (1144)..(1149)
<223> OTHER INFORMATION: SacI, SstI restriction site
<220> FEATURE:
<221> NAME/KEY: misc_feature
<222> LOCATION: (1150)..(1177)

```
<223> OTHER INFORMATION: polylinker
<220> FEATURE:
<221> NAME/KEY: terminator
<222> LOCATION: (1178)..(1382)
<223> OTHER INFORMATION: 35ST

<400> SEQUENCE: 16
atggtggagc acgacactct cgtctactcc aagaatatca agatacagt ctcagaagac      60 caaagggcta ttgagacttt tcaacaaagg gtaatatcgg gaaacctcct cggattccat     120
tgcccagcta tctgtcactt catcaaaagg acagtagaaa aggaaggtgg cacctacaaa     180
tgccatcatt gcgataaagg aaaggctatc gttcaagatg cctctgccga cagtggtccc     240
aaagatggac ccccacccac gaggagcatc gtggaaaaag aagacgttcc aaccacgtct     300
tcaaagcaag tggattgatg tgataacatg gtggagcacg acactctcgt ctactccaag     360
aatatcaaag atacagtctc agaagaccaa agggctattg acttttca acaagggta       420 atatcgggaa acctcctcgg attccattgc ccagctatct gtcacttcat caaaaggaca     480
gtagaaaagg aaggtggcac ctacaaatgc catcattgcg ataaaggaaa ggctatcgtt     540
caagatgcct ctgccgacag tggtcccaaa gatggacccc cacccacgag gagcatcgtg     600 gaaaagaag acgttccaac cacgtcttca agcaagtgg attgatgtga tatctccact       660
gacgtaaggg atgacgcaca atcccactat ccttcgcaag accttcctct atataaggaa     720
gttcatttca tttggagagg acacgctgaa atcaccagtc tctctctaca atctatctc      780 aaataacaaa tctcaacaca acatatacaa aacaaacgaa tctcaagcaa tcaagcattc     840
tacttctatt gcagcaattt aaatcatttc ttttaaagca aaagcaattt tctgaaaatt     900
ttcaccattt acgaacgata gcatctagaa acaatgggat tctttttgtt ttctcaaatg     960
ccttctttct ttcttgtgtc tactcttctt cttttttctta ttatttctca ttcttctcat    1020
gctggtattt tttcatctcg taagtgtaag actccttcta agacttttaa gggttattgc     1080
actagagatt ctaattgtga tacatcttgt agatatgaag gttatcctgc tggtgattaa     1140
taggagctcg gtacccgggg tccgcaaaaa tcaccagtct ctctctacaa atctatctct    1200
ctctattttt ctccagaata atgtgtgagt agttcccaga taagggaatt agggttctta    1260
tagggtttcg ctcatgtgtt gagcatataa gaaaccctta gtatgtattt gtatttgtaa    1320
aatacttcta tcaataaaat ttctaattcc taaaaccaaa atccagtgac ctgcaggcat    1380
gcgagaga                                                              1388

<210> SEQ ID NO 17
<211> LENGTH: 780
<212> TYPE: DNA
<213> ORGANISM: Cauliflower mosaic virus
<220> FEATURE:
<221> NAME/KEY: promoter
<222> LOCATION: (1)..(780)
<223> OTHER INFORMATION: CaMV 35S promoter

<400> SEQUENCE: 17
atggtggagc acgacactct cgtctactcc aagaatatca agatacagt ctcagaagac      60 caaagggcta ttgagacttt tcaacaaagg gtaatatcgg gaaacctcct cggattccat     120
tgcccagcta tctgtcactt catcaaaagg acagtagaaa aggaaggtgg cacctacaaa     180
tgccatcatt gcgataaagg aaaggctatc gttcaagatg cctctgccga cagtggtccc     240
aaagatggac ccccacccac gaggagcatc gtggaaaaag aagacgttcc aaccacgtct     300
tcaaagcaag tggattgatg tgataacatg gtggagcacg acactctcgt ctactccaag     360
```

```
aatatcaaag atacagtctc agaagaccaa agggctattg agactttca acaaagggta    420 atatcgggaa acctcctcgg attccattgc ccagctatct gtcacttcat caaaaggaca    480
gtagaaaagg aaggtggcac ctacaaatgc catcattgcg ataaaggaaa ggctatcgtt    540
caagatgcct ctgccgacag tggtcccaaa gatggacccc cacccacgag gagcatcgtg    600
gaaaaagaag acgttccaac cacgtcttca aagcaagtgg attgatgtga tatctccact    660
gacgtaaggg atgacgcaca atcccactat ccttcgcaag accttcctct atataaggaa    720
gttcatttca tttggagagg acacgctgaa atcaccagtc tctctctaca aatctatctc    780

<210> SEQ ID NO 18
<211> LENGTH: 143
<212> TYPE: DNA
<213> ORGANISM: Tobacco etch virus
<220> FEATURE:
<221> NAME/KEY: enhancer
<222> LOCATION: (1)..(143)
<223> OTHER INFORMATION: TEV 5'UTR translational enhancer

<400> SEQUENCE: 18
aaataacaaa tctcaacaca acatatacaa aacaaacgaa tctcaagcaa tcaagcattc    60
tacttctatt gcagcaattt aaatcatttc ttttaaagca aagcaatttt tctgaaaatt    120
ttcaccattt acgaacgata gca                                             143

<210> SEQ ID NO 19
<211> LENGTH: 205
<212> TYPE: DNA
<213> ORGANISM: Cauliflower mosaic virus
<220> FEATURE:
<221> NAME/KEY: terminator
<222> LOCATION: (1)..(205)
<223> OTHER INFORMATION: CaMV 35S terminator

<400> SEQUENCE: 19
tctctctcta caaatctatc tctctctatt tttctccaga ataatgtgtg agtagttccc    60
agataaggga attagggttc ttatagggtt tcgctcatgt gttgagcata taagaaaccc    120
ttagtatgta tttgtatttg taaaatactt ctatcaataa aatttctaat tcctaaaacc    180
aaaatccagt gacctgcagg catgc                                           205

<210> SEQ ID NO 20
<211> LENGTH: 31
<212> TYPE: DNA
<213> ORGANISM: Artificial Sequence
<220> FEATURE:
<223> OTHER INFORMATION: Zn5 Primer

<400> SEQUENCE: 20
ccaatgcatt gatcttcaaa tgggaatgaa t                                    31

<210> SEQ ID NO 21
<211> LENGTH: 28
<212> TYPE: DNA
<213> ORGANISM: Artificial Sequence
<220> FEATURE:
<223> OTHER INFORMATION: Zn6 Primer

<400> SEQUENCE: 21
aactgcagtt ctaagaccag tcaaacta                                        28

<210> SEQ ID NO 22
```

```
<211> LENGTH: 40
<212> TYPE: DNA
<213> ORGANISM: Artificial Sequence
<220> FEATURE:
<223> OTHER INFORMATION: Fcp Primer

<400> SEQUENCE: 22
ggcctctaga gttatggacg acgagacata gtaattgaag                              40

<210> SEQ ID NO 23
<211> LENGTH: 34
<212> TYPE: DNA
<213> ORGANISM: Artificial Sequence
<220> FEATURE:
<223> OTHER INFORMATION: Rcp Primer

<400> SEQUENCE: 23
gcgcgagctc gatgaaactc caccatcccg atag                                    34

<210> SEQ ID NO 24
<211> LENGTH: 20
<212> TYPE: DNA
<213> ORGANISM: Artificial Sequence
<220> FEATURE:
<223> OTHER INFORMATION: GUSF Primer

<400> SEQUENCE: 24
gtagaaaccc caacccgtga                                                    20

<210> SEQ ID NO 25
<211> LENGTH: 21
<212> TYPE: DNA
<213> ORGANISM: Artificial Sequence
<220> FEATURE:
<223> OTHER INFORMATION: GUSR Primer

<400> SEQUENCE: 25
gcggattcac cacttgcaaa g                                                  21

<210> SEQ ID NO 26
<211> LENGTH: 83
<212> TYPE: PRT
<213> ORGANISM: Artificial Sequence
<220> FEATURE:
<223> OTHER INFORMATION: Variant of SoD2 comprising two additional
      N-terminal amino acids and a Gly33 deletion relative to spinach
      SoD2
<220> FEATURE:
<221> NAME/KEY: signal
<222> LOCATION: (1)..(32)
<223> OTHER INFORMATION: Modified PR-1b signal peptide
<220> FEATURE:
<221> NAME/KEY: mat_peptide
<222> LOCATION: (33)..(83)
<223> OTHER INFORMATION: Putative mature SoD2 peptide with a Gly33
      deletion relative to spinach SoD2

<400> SEQUENCE: 26

Met Gly Phe Phe Leu Phe Ser Gln Met Pro Ser Phe Phe Leu Val Ser
        -30                 -25                 -20

Thr Leu Leu Leu Phe Leu Ile Ile Ser His Ser His Ala Leu Glu
    -15                 -10                  -5              -1

Gly Ile Phe Ser Ser Arg Lys Cys Lys Thr Pro Ser Lys Thr Phe Lys
  1               5                  10                  15

Gly Ile Cys Thr Arg Asp Ser Asn Cys Asp Thr Ser Cys Arg Tyr Glu
                20                  25                  30
```

```
Tyr Pro Ala Gly Asp Cys Lys Gly Ile Arg Arg Arg Cys Met Cys Ser
            35                  40                  45

Lys Pro Cys
    50

<210> SEQ ID NO 27
<211> LENGTH: 265
<212> TYPE: DNA
<213> ORGANISM: Artificial Sequence
<220> FEATURE:
<223> OTHER INFORMATION: Variant of SoD2 comprising two additional
      N-terminal amino acids and a Gly33 deletion relative to spinach
      SoD2
<220> FEATURE:
<221> NAME/KEY: sig_peptide
<222> LOCATION: (8)..(103)
<223> OTHER INFORMATION: PR-1b signal peptide fragment
<220> FEATURE:
<221> NAME/KEY: CDS
<222> LOCATION: (104)..(259)
<223> OTHER INFORMATION: Putative mature SoD2 peptide with a Gly33
      deletion relative to spinach SoD2

<400> SEQUENCE: 27
ttaattaatg ggattctttc tcttttcaca aatgccctca ttctttcttg tgtcgacact      60
tctcttattc ctaataatat ctcactcttc tcatgcgctc gagggaatat tcagctcccg     120
caagtgtaag acgccttcaa agactttcaa agggatatgt acgagagact caaactgtga     180
cacctcatgt cgttacgaat atccggcagg agactgtaaa ggaatacgtc gcagatgtat     240
gtgtagcaag ccttgttaga ggcct                                          265

<210> SEQ ID NO 28
<211> LENGTH: 38
<212> TYPE: PRT
<213> ORGANISM: Artificial Sequence
<220> FEATURE:
<223> OTHER INFORMATION: Core defensin based, in part, on Sod2 and Sod7
<220> FEATURE:
<221> NAME/KEY: VARIANT
<222> LOCATION: (18)..(18)
<220> FEATURE:
<221> NAME/KEY: VARIANT
<222> LOCATION: (18)..(18)
<223> OTHER INFORMATION: Any amino acid

<400> SEQUENCE: 28

Gly Ile Phe Ser Ser Arg Lys Cys Lys Thr Pro Ser Lys Thr Phe Lys
1               5                   10                  15

Gly Xaa Cys Thr Arg Asp Ser Asn Cys Asp Thr Ser Cys Arg Tyr Glu
            20                  25                  30

Gly Tyr Pro Ala Gly Asp
        35

<210> SEQ ID NO 29
<211> LENGTH: 120
<212> TYPE: DNA
<213> ORGANISM: Artificial Sequence
<220> FEATURE:
<223> OTHER INFORMATION: Core defensin based, in part, on Sod2 and Sod7
<220> FEATURE:
<221> NAME/KEY: variation
<222> LOCATION: (52)..(52)
<223> OTHER INFORMATION: t, any other base, or absent (e.g., if 53 and
      54 are also absent)
<220> FEATURE:
<221> NAME/KEY: misc_feature
<222> LOCATION: (52)..(54)
<223> OTHER INFORMATION: n is a, c, g, or t
```

```
<220> FEATURE:
<221> NAME/KEY: variation
<222> LOCATION: (53)..(53)
<223> OTHER INFORMATION: a, any other base, or absent (e.g., if 52 and
      54 are also absent)
<220> FEATURE:
<221> NAME/KEY: variation
<222> LOCATION: (54)..(54)
<223> OTHER INFORMATION: t, any other base, or absent (e.g., if 52 and
      53 are also absent)

<400> SEQUENCE: 29
ggaattttct cttcaaggaa gtgcaagact ccatctaaga ctttcaaggg annntgtact      60
agggattcta actgcgatac atcatgcaga tacgagggct atcctgctgg cgattaataa    120

<210> SEQ ID NO 30
<211> LENGTH: 174
<212> TYPE: DNA
<213> ORGANISM: Artificial Sequence
<220> FEATURE:
<223> OTHER INFORMATION: SoD2 codon-optimized with DNA 2.0

<400> SEQUENCE: 30
tctagaatgg gaatcttcag ttcgagaaag tgtaaaaccc cctcaaaaac attcaaaggt      60
atttgcacga gagattctaa ttgcgatact agctgccgtt atgagggtta ccctgctggc    120
gactgtaagg ggataaggag gagatgtatg tgctccaagc catgttaagg tacc          174

<210> SEQ ID NO 31
<211> LENGTH: 132
<212> TYPE: DNA
<213> ORGANISM: Artificial Sequence
<220> FEATURE:
<223> OTHER INFORMATION: SoD7 codon-optimized with DNA 2.0

<400> SEQUENCE: 31
tctagaatgg gtatcttctc aagcagaaag tgcaaaacac cttctaaaac ctttaaggga      60
tattgtacta gggactccaa ttgtgatacg agttgccgtt acgagggcta tccagctggg    120
gattaaggta cc                                                        132
```

PATHOGEN RESISTANT CITRUS COMPOSITIONS, ORGANISMS, SYSTEMS, AND METHODS

CROSS-REFERENCE TO RELATED APPLICATIONS

This application claims priority to U.S. patent application Ser. No. 13/751,936, filed on Jan. 28, 2013, which claims priority from U.S. Provisional Patent Application 61/591,680, filed on Jan. 27, 2012 and U.S. Provisional Patent Application 61/641,641, filed on May 2, 2012. The contents of all of the above are hereby incorporated in their entirety by reference.

FIELD OF THE DISCLOSURE

The present disclosure relates, in some embodiments, to pathogen resistant *citrus* compositions, organisms, systems, and methods.

BACKGROUND OF THE DISCLOSURE

At present, there are no *Citrus* cultivars resistant to bacterial canker (*Xanthomonas axonopodis* pv. *citri*) (Xac), and/or *citrus* Huanglongbing (ex greening) caused by *Candidatus Liberibacter asiaticus* (Las). Indeed, no genetic resistance to these microbial pathogens has ever been found within the *Citrus* genus. Conventional cross-breeding efforts to produce resistant cultivars have been hindered by the complex reproductive biology and long life cycle of *Citrus* spp.

SUMMARY

Accordingly, a need has arisen for plants (e.g., *citrus*) with improved resistance to disease. A further need has arisen for improved methods, compositions, and systems for preparing genetically modified plants (e.g., *citrus*).

The present disclosure relates, according to some embodiments, to pathogen resistant *citrus* compositions, organisms, systems, and methods. For example, a composition may comprise a nucleic acid (e.g., a defensin nucleic acid). In some embodiments, a nucleic acid may comprise a nucleic acid sequence (a) having from about 75% to about 100% identity (e.g., about 98% identity) to a defensin sequence (e.g., SEQ ID NOS: 3, 4, 5, 6, 9, 10, 11, 12, and/or 29) and/or (b) encoding an amino acid sequence having from about 95% to about 100% identity (e.g., 98% identity) to SEQ ID NOS: 1, 2, 7, 8, and/or 28. A nucleic acid may comprise, in some embodiments, a nucleic acid sequence having about 98% identity to a sequence selected from the group consisting of SEQ ID NO: 3 and SEQ ID NO: 5 and encoding a peptide having an amino acid sequence having at least about 99% identity to SEQ ID NO: 1. A nucleic acid may comprise, in some embodiments, a nucleic acid sequence having about 98% identity to a sequence selected from the group consisting of SEQ ID NO: 4 and SEQ ID NO: 6 and encoding a peptide having an amino acid sequence having at least about 99% identity to SEQ ID NO: 2. According to some embodiments, a nucleic acid may comprise a nucleic acid sequence having about 98% identity to a sequence selected from the group consisting of SEQ ID NO: 9 and SEQ ID NO: 11 and encoding a peptide having an amino acid sequence having at least about 99% identity to SEQ ID NO: 7. A nucleic acid may comprise a nucleic acid sequence having about 98% identity to a sequence selected from the group consisting of SEQ ID NO: 10 and SEQ ID NO: 12 and encoding a peptide having an amino acid sequence having at least about 99% identity to SEQ ID NO: 8, in some embodiments.

The present disclosure relates, in some embodiments, to defensin expression vectors operable in *citrus*. For example, an expression vector may comprise, in a 5' to 3' direction, (a) an expression control sequence; (b) an expressable nucleic acid (e.g., a nucleic acid encoding an exogenous polypeptide) operably linked to the expression control sequence; and (c) a 3' termination sequence operably linked to the expressable nucleic acid. In some embodiments, an exogenous nucleic acid may comprise a nucleic acid sequence having at least about 75% identity (e.g., at least about 98% identity) to a nucleic acid sequence selected from the group consisting of SEQ ID NO: 3, SEQ ID NO: 4, SEQ ID NO: 5, SEQ ID NO: 6, SEQ ID NO: 9, SEQ ID NO: 10, SEQ ID NO: 11, SEQ ID NO: 12, and SEQ ID NO: 29. An expression vector may be located in a bacterial cell or a plant cell according to some embodiments. An expression vector may comprise, in some embodiments, the nucleotide sequence AACAATGG at positions −4 to 4 relative to a coding sequence (e.g., encoded by an exogenous nucleic acid sequence). According to some embodiments, an expression vector may comprise a linker (e.g., 3' of the expression control sequence and/or 5' of the nucleic acid (e.g., a nucleic acid encoding an exogenous polypeptide) having a length of from about 1 to about 200 nucleotides.

The present disclosure relates, in some embodiments, to a bacterial cell comprising an expression vector. For example, a bacterial cell may comprise an expression vector comprising, in a 5' to 3' direction, (a) an expression control sequence; (b) an expressable nucleic acid (e.g., a nucleic acid encoding an exogenous polypeptide) operably linked to the expression control sequence; and (c) a 3' termination sequence operably linked to the expressable nucleic acid. A bacterial cell may comprise, for example, an expression vector comprising, in a 5' to 3' direction, (a) an expression control sequence; (b) an exogenous nucleic acid operably linked to the expression control sequence; and/or (c) a 3' termination sequence operably linked to the exogenous nucleic acid, wherein the exogenous nucleic acid comprises a nucleic acid sequence having at least about 98% identity to a nucleic acid sequence selected from the group consisting of SEQ ID NO: 3, SEQ ID NO: 4, SEQ ID NO: 5, SEQ ID NO: 6, SEQ ID NO: 9, SEQ ID NO: 10, SEQ ID NO: 11, and SEQ ID NO: 12.

The present disclosure relates, in some embodiments, to a plant cell (e.g., a *citrus* plant cell) comprising an expression vector. For example, a plant cell (e.g., a *citrus* plant cell) may comprise an expression vector comprising, in a 5' to 3' direction, (a) an expression control sequence; (b) an expressable nucleic acid (e.g., a nucleic acid encoding an exogenous polypeptide) operably linked to the expression control sequence; and (c) a 3' termination sequence operably linked to the expressable nucleic acid. A plant cell (e.g., a *citrus* plant cell) may comprise, for example, an expression vector comprising, in a 5' to 3' direction, (a) an expression control sequence; (b) an exogenous nucleic acid operably linked to the expression control sequence; and/or (c) a 3' termination sequence operably linked to the exogenous nucleic acid, wherein the exogenous nucleic acid comprises a nucleic acid sequence having at least about 98% identity to a nucleic acid sequence selected from the group consisting of SEQ ID NO: 3, SEQ ID NO: 4, SEQ ID NO: 5, SEQ ID NO: 6, SEQ ID NO: 9, SEQ ID NO: 10, SEQ ID NO: 11, SEQ ID NO: 12, and SEQ ID NO: 29. A plant cell (e.g., a *citrus* plant cell) may be located in a plant (e.g., a *citrus* plant) according to some embodiments. Examples of *citrus* plants include, without limitation, orange and grapefruit. A plant cell may comprise a defensin peptide. A defensin peptide may have, in some embodiments, an amino acid sequence having at least about 99% identity to SEQ ID NO: 1, SEQ ID NO: 2, SEQ ID NO: 7, SEQ ID NO: 8 or SEQ ID NO: 28 (e.g., encoded by and/or expressed from an expression vector nucleic acid) according to some embodiments.

In some embodiments, the present disclosure relates to a *citrus* plant (e.g., orange and/or grapefruit) comprising an expression vector. A *citrus* plant may comprise an expression vector in a single cell, a plurality of cells (e.g., mosaic), or in all cells. A mosaic plant may arise from a graft in some embodiments. For example, a *citrus* plant may comprise a graft of a transgenic plant having an expression vector in all cells (e.g., scion) and a plant having a different expression vector or no expression vector in its cells (e.g., rootstock). A *citrus* plant may comprise, in some embodiments, in a single cell, a plurality of cells (e.g., mosaic), or in all cells a first expression vector (e.g., encoding a first defensin peptide) and in a single cell, a plurality of cells (e.g., mosaic), or in all cells a second expression vector (e.g., encoding a second defensin peptide). For example, a *citrus* plant cell may comprise (a) a first expression vector, the first expression vector comprising, in a 5' to 3' direction, (i) a first expression control sequence; (ii) a first exogenous nucleic acid operably linked to the first expression control sequence; and (iii) a first 3' termination sequence operably linked to the first exogenous nucleic acid, wherein the first exogenous nucleic acid comprises a nucleic acid sequence having at least about 98% identity to a nucleic acid sequence selected from the group consisting of SEQ ID NO: 3, SEQ ID NO: 5, SEQ ID NO: 9, and SEQ ID NO: 11; and (b) a second expression vector, the second expression vector comprising, in a 5' to 3' direction, (iv) a second expression control sequence; (v) a second exogenous nucleic acid operably linked to the second expression control sequence; and (vi) a second 3' termination sequence operably linked to the second exogenous nucleic acid, wherein the second exogenous nucleic acid comprises a nucleic acid sequence having at least about 98% identity to a nucleic acid sequence selected from the group consisting of SEQ ID NO: 4, SEQ ID NO: 6, SEQ ID NO: 10, and SEQ ID NO: 12. According to some embodiments, a *citrus* plant may comprise in a single cell, a plurality of cells (e.g., mosaic), or in all cells an expression vector comprising a first nucleic acid sequence encoding a first defensin peptide (e.g., SoD2) and a second nucleic acid sequence encoding a second defensin peptide (e.g., SoD7). In some embodiments, a *citrus* plant may comprise a defensin peptide in a single cell, a plurality of cells (e.g., mosaic), or in all cells. A *citrus* plant may comprise in a single cell, a plurality of cells (e.g., mosaic), or in all cells a first defensin peptide (e.g., a peptide having at least about 99% identity to SEQ ID NO: 1 or SEQ ID NO: 7) and in a single cell, a plurality of cells (e.g., mosaic), or in all cells a second defensin peptide (e.g., a peptide having at least about 99% identity to SEQ ID NO: 2 or SEQ ID NO: 8).

The present disclosure relates, in some embodiments, to methods of expressing in a *citrus* plant an exogenous nucleic acid comprising a nucleic acid sequence encoding an expressed peptide (e.g., a defensin peptide). For example, a method may comprise contacting an expression cassette comprising an exogenous nucleic acid or an expression vector comprising an exogenous nucleic acid with the cytosol of a cell of a *citrus* plant under conditions that permit expression of the exogenous nucleic acid and formation of the expressed peptide. In some embodiments, an exogenous nucleic acid may comprise a nucleic acid sequence having at least 98% identity to a nucleic acid sequence selected from SEQ ID NO: 3, SEQ ID NO: 4, SEQ ID NO: 5, SEQ ID NO: 6, SEQ ID NO: 9, SEQ ID NO: 10, SEQ ID NO: 11, SEQ ID NO: 12, and/or SEQ ID NO: 29. In some embodiments, an expression vector and/or an expression cassette may comprise, in a 5' to 3' direction, an expression control sequence, the exogenous nucleic acid operably linked to the expression control sequence, and a 3' termination sequence operably linked to the exogenous nucleic acid. An expressed peptide may comprise an amino acid sequence having at least 99% identity to an amino acid sequence selected from SEQ ID NO: 1, SEQ ID NO: 2, SEQ ID NO: 7, SEQ ID NO: 8, and/or SEQ ID NO: 28 according to some embodiments. Contacting an expression vector or cassette may further comprise, in some embodiments, co-cultivating the cell with an *Agrobacterium* cell comprising the expression vector or expression cassette to form a co-cultivated plant cell. According to some embodiments, a plant may be regenerated from a co-cultivated plant cell.

The present disclosure relates, in some embodiments, to methods for treating a *citrus* plant having and/or at risk of having a microbial infection (e.g., bacterial canker (*Xanthomonas axonopodis* pv. *citri*) (Xac), and/or citrus Huanglongbing (ex greening) caused by *Candidatus Liberibacter asiaticus* (Las)). For example, a method may comprise forming in the *citrus* plant at least one defensin peptide. Forming in the *citrus* plant at least one defensin peptide may comprise, in some embodiments, grafting the *citrus* plant with a cutting (e.g., a scion or a rootstock) from a second *citrus* plant, the second *citrus* plant comprising an expression vector and/or an expression cassette comprising, in a 5' to 3' direction, an expression control sequence, a defensin nucleic acid operably linked to the expression control sequence, and a 3' termination sequence operably linked to the defensin nucleic acid, wherein the defensin nucleic acid comprises a nucleic acid sequence encoding an amino acid sequence having at least 99% identity to an amino acid sequence selected from SEQ ID NO: 1, SEQ ID NO: 2, SEQ ID NO: 7, SEQ ID NO: 8, and/or SEQ ID NO: 28 under conditions that permit expression of the defensin nucleic acid.

BRIEF DESCRIPTION OF THE DRAWINGS

Some embodiments of the disclosure may be understood by referring, in part, to the present disclosure and the accompanying drawings, wherein:

FIG. 15A illustrates the percentage of Generation 2 *citrus* plants infected upon the first, second, and third sampling of challenged material, according to specific example embodiments of the disclosure;

FIG. 15B is a continuation of the bar graph of FIG. 15A illustrating the percentage of Generation 2 *citrus* plants infected upon the first, second, and third sampling of challenged material, according to specific example embodiments of the disclosure;

FIG. 15C is a continuation of the bar graph of FIG. 15A illustrating the percentage of Generation 2 *citrus* plants infected upon the first, second, and third sampling of challenged material, according to specific example embodiments of the disclosure;

FIG. 16A illustrates the percentage of Generations 2 and 3 *citrus* plants infected upon the first, second and third samplings of challenged material, according to specific example embodiments of the disclosure;

FIG. 16B is a continuation of the bar graph of FIG. 16A illustrating the percentage of Generations 2 and 3 *citrus* plants infected upon the first, second and third samplings of challenged material, according to specific example embodiments of the disclosure;

FIG. 16C is a continuation of the bar graph of FIG. 16A illustrating the percentage of Generations 2 and 3 *citrus* plants infected upon the first, second and third samplings of challenged material, according to specific example embodiments of the disclosure.

BRIEF DESCRIPTION OF THE SEQUENCE LISTING

Figure 1:
FIG. 1 illustrates an *Agrobacterium* transformation construct comprising a nucleic acid encoding SoD2 according to specific example embodiments of the disclosure.

Some embodiments of the disclosure may be understood by referring, in part, to the present disclosure and the accompanying sequence listing, wherein:

SEQ ID NO: 1 illustrates an amino acid sequence of a spinach (*Spinacia oleracea*) defensin (SoD2) according to a specific example embodiment of the disclosure;

SEQ ID NO: 2 illustrates an amino acid sequence of a spinach (*Spinacia oleracea*) defensin (SoD7) according to a specific example embodiment of the disclosure;

SEQ ID NO: 3 illustrates a GenScript-optimized nucleic acid sequence for expression of a spinach (*Spinacia oleracea*) defensin (SoD2) according to a specific example embodiment of the disclosure;

SEQ ID NO: 4 illustrates a GenScript-optimized nucleic acid sequence for expression of a spinach (*Spinacia oleracea*) defensin (SoD7) according to a specific example embodiment of the disclosure;

SEQ ID NO: 5 illustrates a CODA-optimized nucleic acid sequence for expression of a spinach (*Spinacia oleracea*) defensin (SoD2) according to a specific example embodiment of the disclosure;

SEQ ID NO: 6 illustrates a CODA-optimized nucleic acid sequence for expression of a spinach (*Spinacia oleracea*) defensin (SoD7) according to a specific example embodiment of the disclosure;

SEQ ID NO: 7 illustrates an amino acid sequence of a chimeric peptide comprising a PR-1b signal peptide and a spinach (*Spinacia oleracea*) defensin (SoD2) according to a specific example embodiment of the disclosure;

SEQ ID NO: 8 illustrates an amino acid sequence of a chimeric peptide comprising a PR-1b signal peptide and a spinach (*Spinacia oleracea*) defensin (SoD7) according to a specific example embodiment of the disclosure;

SEQ ID NO: 9 illustrates a chimeric nucleic acid sequence comprising a nucleic acid sequence encoding a PR-1b signal peptide and a GenScript-optimized nucleic acid sequence for expression of a spinach (*Spinacia oleracea*) defensin (SoD2) according to a specific example embodiment of the disclosure;

SEQ ID NO: 10 illustrates a chimeric nucleic acid sequence comprising a nucleic acid sequence encoding a PR-1b signal peptide and a GenScript-optimized nucleic acid sequence for expression of a spinach (*Spinacia oleracea*) defensin (SoD7) according to a specific example embodiment of the disclosure;

SEQ ID NO: 11 illustrates a chimeric nucleic acid sequence comprising a nucleic acid sequence encoding a PR-1b signal peptide and a CODA-optimized nucleic acid sequence for expression of a spinach (*Spinacia oleracea*) defensin (SoD2) according to a specific example embodiment of the disclosure;

SEQ ID NO: 12 illustrates a chimeric nucleic acid sequence comprising a nucleic acid sequence encoding a PR-1b signal peptide and a CODA-optimized nucleic acid sequence for expression of a spinach (*Spinacia oleracea*) defensin (SoD7) according to a specific example embodiment of the disclosure;

SEQ ID NO: 13 illustrates an expression cassette comprising a nucleic acid sequence encoding a PR-1b signal peptide and a GenScript-optimized nucleic acid sequence for expression of a spinach (*Spinacia oleracea*) defensin (SoD2) according to a specific example embodiment of the disclosure;

SEQ ID NO: 14 illustrates an expression cassette comprising a nucleic acid sequence encoding a PR-1b signal peptide and a GenScript-optimized nucleic acid sequence for expression of a spinach (*Spinacia oleracea*) defensin (SoD7) according to a specific example embodiment of the disclosure;

SEQ ID NO: 15 illustrates an expression cassette comprising a nucleic acid sequence encoding a PR-1b signal peptide and a CODA-optimized nucleic acid sequence for expression of a spinach (*Spinacia oleracea*) defensin (SoD2) according to a specific example embodiment of the disclosure;

SEQ ID NO: 16 illustrates an expression cassette comprising a nucleic acid sequence encoding a PR-1b signal peptide and a CODA-optimized nucleic acid sequence for expression of a spinach (*Spinacia oleracea*) defensin (SoD7) according to a specific example embodiment of the disclosure;

SEQ ID NO: 17 illustrates an expression control sequence (CaMV 35S promoter) according to a specific example embodiment of the disclosure;

SEQ ID NO: 18 illustrates an untranslated region (TEV 5'UTR) according to a specific example embodiment of the disclosure;

SEQ ID NO: 19 illustrates an expression control sequence (CaMV 35S terminator) according to a specific example embodiment of the disclosure;

SEQ ID NO: 20 illustrates a nucleic acid sequence of a primer designated Zn5 according to a specific example embodiment of the disclosure;

SEQ ID NO: 21 illustrates a nucleic acid sequence of a primer designated Zn6 according to a specific example embodiment of the disclosure;

SEQ ID NO: 22 illustrates a nucleic acid sequence of a primer designated Fcp according to a specific example embodiment of the disclosure;

SEQ ID NO: 23 illustrates a nucleic acid sequence of a primer designated Rcp according to a specific example embodiment of the disclosure;

SEQ ID NO: 24 illustrates a nucleic acid sequence of a primer designated GUSF according to a specific example embodiment of the disclosure;

SEQ ID NO: 25 illustrates a nucleic acid sequence of a primer designated GUSR according to a specific example embodiment of the disclosure;

SEQ ID NO: 26 illustrates an amino acid sequence of a chimeric peptide comprising a modified PR-1b signal peptide and a GenScript-optimized nucleic acid sequence having a single deletion for expression of a spinach (*Spinacia oleracea*) defensin (SoD2) according to a specific example embodiment of the disclosure;

SEQ ID NO: 27 illustrates a chimeric nucleic acid sequence comprising a nucleic acid sequence encoding a modified PR-1b signal peptide and a GenScript-optimized nucleic acid sequence having a single deletion for expression of a spinach (*Spinacia oleracea*) defensin (SoD2) according to a specific example embodiment of the disclosure;

SEQ ID NO: 28 illustrates a core amino acid sequence of a defensin according to a specific example embodiment of the disclosure;

SEQ ID NO: 29 illustrates a nucleic acid sequence for expression of a core defensin according to a specific example embodiment of the disclosure;

SEQ ID NO: 30 illustrates a DNA 2.0-optimized nucleic acid sequence for expression of a spinach (*Spinacia oleracea*) defensin (SoD2) according to a specific example embodiment of the disclosure; and SEQ ID NO: 31 illustrates a DNA 2.0-optimized nucleic acid sequence for expression of a spinach (*Spinacia oleracea*) defensin (SoD7) according to a specific example embodiment of the disclosure.

DETAILED DESCRIPTION

The present disclosure relates, in some embodiments, to compositions, organisms, systems, and methods for enhancing a plant's innate ability, if any, to respond to contact (e.g., infection) with a pathogen (e.g., bacteria, yeast, fungus, virus). In some embodiments, the present disclosure relates to compositions, organisms, systems, and methods for expressing a gene product (e.g., an antimicrobial peptide) in a plant (e.g., *citrus*). For example, the present disclosure relates to expression control sequences (e.g., promoters), expression cassettes, expression vectors, microorganisms, and/or plants comprising one or more antimicrobial peptides and/or one or more nucleic acids encoding one or more antimicrobial peptides.

I. Compositions

A. Antimicrobial Peptides

The present disclosure relates, according to some embodiments, to peptides and/or proteins having insecticidal activity, antimicrobial activity, and/or antiviral activity, which may include, without limitation, avidin, vegetative insecticidal proteins (e.g., Vip3A), insecticidal crystal proteins from *Bacillus thuringiensis* (e.g., Cry1, Cry1Ab, Cry2, Cry9), pea albumin (e.g., PA1b), hirsutellin A, lectins (e.g., snow drop lily lectin, garlic lectin, onion lectin), amylase inhibitors (e.g., alpha amylase inhibitor), arcelins (e.g., arcelins from beans), proteinase inhibitors, lysozymes (e.g., bovine lysozyme, human lysozyme, mollusk lysozyme), defensin (e.g., SoD2 and/or SoD7), chitinase, β-1,3-glucanase, variants thereof, and/or combinations thereof. An antimicrobial peptide may comprise, for example, one or more antimicrobial-peptides belonging to the family of plant defensins. These polypeptides were originally isolated from spinach leaves (*Spinacia oleracea*). In some embodiments, a defensin may be small (about 5 kDa), may be basic and/or may be cysteine-rich. In some embodiments, a defensin may comprise a peptide having an amino acid sequence sharing at least about 95% identity, at least about 96% identity, at least about 97% identity, at least about 98% identity, at least about 99% identity, and/or about 100% identity with SEQ ID NO: 1 and/or SEQ ID NO: 2. In some embodiments, an antimicrobial peptide may further comprise one or more amino acids that are independently and/or collectively either neutral (e.g., do not adversely impact antibacterial functionality) and/or augment antibacterial functionality (e.g., by directing the peptide to a desired location (e.g., cellular and/or extracellular). For example, a defensin may comprise a signal peptide derived from the tobacco pathogenesis-related (PR)-1b protein that allows the transport of the peptides into the apoplast of plant cells (e.g., via the secretory pathway) and/or accumulation in the intercellular spaces of leaves, stems, flowers, fruits, seeds, and/or roots. A defensin may comprise, according to some embodiments, a peptide having an amino acid sequence sharing at least about 95% identity, at least about 96% identity, at least about 97% identity, at least about 98% identity, at least about 99% identity, and/or about 100% identity with SEQ ID NO: 7 and/or SEQ ID NO: 8.

B. Nucleic Acids

The present disclosure relates, in some embodiments, to nucleic acids (e.g., cassettes, vectors) comprising one or more sequences encoding one or more antimicrobial peptides. For example, a nucleic acid may comprise a cassette comprising a synthetic nucleic acid sequence of SoD2 and/or SoD7 genes. Synthetic SoD2 and/or SoD7 codons may specify the same amino acid sequences as native spinach, having their codons optimized for *citrus* codon usage. A nucleic acid comprising a SoD2 and/or SoD7 coding sequence may comprise a sequence encoding a signal peptide (e.g., PR-1b). In some embodiments, expression of a nucleic acid comprising a sequence encoding an antimicrobial peptide may be optimized by positioning an initiation codon in a favorable (e.g., optimal) 5' context. According to some embodiments, a nucleic acid may comprise an expression control sequence (e.g., operably linked to a coding sequence). For example, a nucleic acid may comprise a coding gene sequence under the control of a dual enhanced CaMV 35S promoter with a 5' UTR from TEV plant potyvirus (e.g., to provide a translation-enhancing activity to the defensin genes).

According to some embodiments, a nucleic acid may comprise a nucleotide sequence having at least about 75% identity to SEQ ID NOS: 3, 4, 5, 6, 9, 10, 11, 12, 29, 30, and/or 31, at least about 80% identity to SEQ ID NOS: 3, 4, 5, 6, 9, 10, 11, 12, 29, 30, and/or 29, at least about 85% identity to SEQ ID NOS: 3, 4, 5, 6, 9, 10, 11, 12, 29, 30, and/or 31, at least about 90% identity to SEQ ID NOS: 3, 4, 5, 6, 9, 10, 11, 12, 29, 30, and/or 31, at least about 95% identity to SEQ ID NOS: 3, 4, 5, 6, 9, 10, 11, 12, 29, 30, and/or 31, at least about 97% identity to SEQ ID NOS: 3, 4, 5, 6, 9, 10, 11, 12, 29, 30, and/or 31, at least about 98% identity to SEQ ID NOS: 3, 4, 5, 6, 9, 10, 11, 12, 29, 30, and/or 31, at least about 99% identity to SEQ ID NOS: 3, 4, 5, 6, 9, 10, 11, 12, 29, 30, and/or 31, and/or about 100% identity to SEQ ID NOS: 3, 4, 5, 6, 9, 10, 11, 12, 29, 30, and/or 31. A nucleotide sequence may encode, in some embodiments, an amino acid sequence having at least about 98% identity to SEQ ID NOS: 1, 2, 7, 8, and/or 28, at least about 99% identity to SEQ ID NOS: 1, 2, 7, 8, and/or 28, and/or about 100% identity to SEQ ID NOS: 1, 2, 7, 8, and/or 28. According to some embodiments, a nucleic acid may have a first measure of sequence identity to a reference nucleic acid sequence and may encode an amino acid sequence having a second measure of sequence identity to a reference amino acid sequence. For example, a nucleic acid may have about 85% identity to SEQ ID NOS: 3, 4, 5, 6, 9, 10, 11, 12, 29, 30, and/or 31 and encode an amino acid sequence having about 100% identity with SEQ ID NOS: 1, 2, 7, 8, and/or 28, according to some embodiments.

A nucleic acid sequence, according to some embodiments, may hybridize to a nucleic acid having the nucleotide sequence of SEQ ID NOS: 3, 4, 5, 6, 9, 10, 11, 12, 29, 30, and/or 31 under stringent conditions. Stringent conditions may include, for example, (a) 4×SSC at 65° C. followed by 0.1×SSC at 65° for 60 minutes and/or (b) 50% formamide, 4×SSC at 65° C. A nucleic acid may comprise a deletion fragment (e.g., a deletion of from about 1 to about 12 bases) of a nucleic acid having a sequence of SEQ ID NOS: 3, 4, 5, 6, 9, 10, 11, 12, 29, 30, and/or 31 that retains antimicrobial activity against at least one microorganism capable of infecting a *citrus* plant. One of ordinary skill in the art having the benefit of the present disclosure may prepare one or more deletion fragments of a nucleic acid having a sequence of SEQ ID NOS: 3, 4, 5, 6, 9, 10, 11, 12, 29, 30, and/or 31 and screen the resulting fragments for antimicrobial activity against at least one microorganism capable of infecting a *citrus* plant.

A nucleic acid sequence having a sequence like SEQ ID NOS: 3, 4, 5, 6, 30, and/or 31 may be identified by database searches using the sequence or elements thereof as the query sequence using the Gapped BLAST algorithm (Altschul et al., 1997 *Nucl. Acids Res.* 25:3389-3402) with the BLOSUM62 Matrix, a gap cost of 11 and persistence cost of 1 per residue and an E value of 10. Sequence identity may be assessed by any available method according to some embodiments. For example, two sequences may be compared with either ALIGN (Global alignment) or LALIGN (Local homology alignment) in the FASTA suite of applications (Pearson and Lipman, 1988 *Proc. Nat. Acad. Sci.* 85:2444-2448; Pearson, 1990 *Methods in Enzymology* 183: 63-98) with the BLOSUM50 matrix and gap penalties of −16, −4. Sequence similarity may be assessed according to ClustalW (Larkin et al., 2007, *Bioinformatics* 23(21): 2947-2948), BLAST, FASTA or similar algorithm.

C. Expression Cassettes and Vectors

The disclosure relates, in some embodiments, to expression vectors and/or expression cassettes for expressing a nucleic acid sequence (e.g., a coding sequence) in a cell and comprising an expression control sequence and the nucleic acid sequence operably linked to the expression control sequence. Thus, for example, an expression cassette may comprise a heterologous coding sequence, the expression of which may be desired in a plant.

1. Expression Vectors

The disclosure relates, in some embodiments, to an expression vector which may comprise, for example, a nucleic acid having an expression control sequence and a coding sequence operably linked to the expression control sequence. In some embodiments, an expression control sequence may comprise one or more promoters, one or more operators, one or more enhancers, one or more ribosome binding sites, and/or combinations thereof. An expression control sequence may comprise, for example, a nucleic acid having promoter activity. An expression control sequence, according to some embodiments, may be constitutively active or conditionally active in (a) an organ selected from root, leaf, stem, flower, seed, and/or fruit, and/or (b) active in a tissue selected from epidermis, periderm, parenchyma, collenchyma, sclerenchyma, xylem, phloem, and/or secretory structures. An expression control sequence, according to some embodiments, may be operable to drive expression of a nucleic acid sequence (e.g., a coding sequence) in a cell. Metrics for expression may include, for example, rate of appearance and/or accumulation of a gene product (e.g., RNA and/or protein) and/or total accumulation of a gene product as of one or more time points (e.g., elapsed time after a starting point and/or a stage of development). Comparative assays for gene products may be qualitative, semi-quantitative, and/or quantitative in some embodiments. Comparative assays may indirectly and/or directly assess the presence and/or amount of gene product. In some embodiments, an expression control sequence may be sensitive to one or more stimuli (e.g., one or more small molecules, one or more plant defense-inducing agents, mechanical damage, temperature, pressure). For example, activity of an expression control sequence may be enhanced or suppressed upon infection with a microorganism (e.g., a bacteria or a virus).

Figure 2:
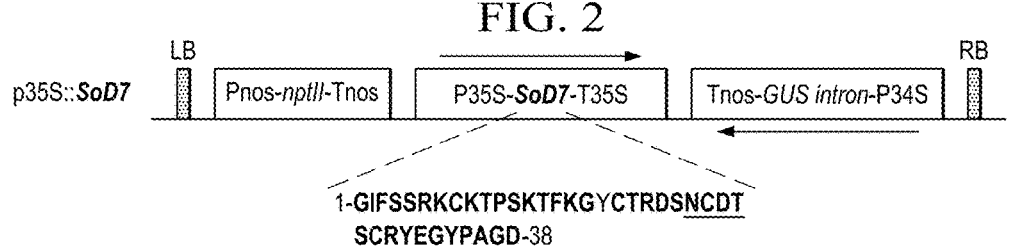
FIG. 2 illustrates an *Agrobacterium* transformation construct comprising a nucleic acid encoding SoD7 according to specific example embodiments of the disclosure.

An expression vector may be contacted with a cell (e.g., a plant cell) under conditions that permit expression (e.g., transcription) of the coding sequence. Examples of expression vectors may include the *Agrobacterium* transformation constructs shown in FIG. 1 and FIG. 2. An expression control sequence may be contacted with a plant cell (e.g., an embryonic cell, a stem cell, a callous cell) under conditions that permit expression of the coding sequence in the cell and/or cells derived from the plant cell according to some embodiments. An expression vector may be contacted with a cell (e.g., a plant cell), in some embodiments, under conditions that permit inheritance of at least a portion of the expression vector in the cell's progeny. According to some embodiments, an expression vector may include one or more selectable markers. For example, an expression vector may include a marker for selection when the vector is in a bacterial host, a yeast host, and/or a plant host.

2. Expression Cassettes

According to some embodiments, the disclosure relates to an expression cassette which may comprise, for example, a nucleic acid having an expression control sequence and a coding sequence operably linked to the expression control sequence. An expression cassette may be comprised in an expression vector. A coding sequence, in some embodiments, may comprise any coding sequence expressible in at least one plant cell. For example, a coding sequence may comprise a plant sequence, a yeast sequence, a bacterial sequence, a viral sequence (e.g., plant virus), an artificial sequence, an antisense sequence thereof, a fragment thereof, a variant thereof, and/or combinations thereof. A coding sequence may comprise, in some embodiments, a sequence encoding one or more gene products with insecticidal, antibacterial, antifungal, antimicrobial, and/or antiviral activity. A coding sequence may comprise, in some embodiments, a start codon, an intron, and/or a translation termination sequence. According to some embodiments, a coding sequence may comprise one or more natural or artificial coding sequences (e.g., encoding a single protein or a chimera). According to some embodiments, an expression cassette may optionally comprise a termination sequence. A coding sequence, in some embodiments, may comprise a sequence at least partially codon optimized for expression in an organism of interest (e.g., a *citrus* plant).

An expression control sequence may be used, in some embodiments, to construct an expression cassette comprising, in the 5' to 3' direction, (a) the expression control sequence, (b) a heterologous gene or a coding sequence, or sequence complementary to a native plant gene under control of the expression control sequence, and/or (c) a 3' termination sequence (e.g., a termination sequence comprising a polyadenylation site). Examples of expression cassettes may include, in some embodiments, the cassettes shown in SEQ ID NOS: 13-16. An expression cassette may be incorporated into a variety of autonomously replicating vectors in order to construct an expression vector. An expression cassette may be constructed, for example, by ligating an expression control sequence to a sequence to be expressed (e.g., a coding sequence).

Some techniques for construction of expression cassettes are well known to those of ordinary skill in the art. For example, a variety of strategies are available for ligating fragments of DNA, the choice of which depends on the nature of the termini of the DNA fragments. An artisan of ordinary skill having the benefit of the present disclosure, a coding sequence (e.g., having antimicrobial activity) and/or portions thereof may be provided by other means, for example chemical or enzymatic synthesis. A nucleic acid may comprise, in a 5' to 3' direction, an expression control sequence, a linker (optional), and a coding sequence according to some embodiments. A nucleic acid may comprise, in some embodiments, one or more restriction sites and/or junction sites between an expression control sequence, a linker, and/or a coding sequence.

II. Microorganisms

The present disclosure relates, in some embodiments, to a microorganism comprising an antimicrobial peptide (e.g., a heterologous antimicrobial peptide) and/or a nucleic acid (e.g., a heterologous and/or expressible nucleic acid) comprising a nucleic acid sequence encoding an antimicrobial peptide. For example, a microorganism may comprise a bacteria, a yeast, and/or a virus. Examples of microorganisms may include, without limitation, *Agrobacterium tumefaciens*, *Escherichia coli*, a lepidopteran cell line, a Rice tungro bacilliform virus, a Commelina yellow mosaic virus, a Banana streak virus, a Taro bacilliform virus, and/or baculovirus. According to some embodiments, an antimicrobial peptide may be tolerated by and/or innocuous to its host microorganism. A microorganism may comprise an expression control sequence and an antimicrobial peptide coding sequence operably linked to the expression control sequence. A nucleic acid (e.g., a heterologous and/or expressible nucleic acid) comprising a nucleic acid sequence encoding an antimicrobial peptide may be present, in some embodiments, on a genomic nucleic acid and/or an extra-genomic nucleic acid.

III. Plants

The present disclosure relates, in some embodiments, to a plant cell (e.g., an embryonic cell, a stem cell, a callous cell), a tissue, and/or a plant comprising an antimicrobial peptide (e.g., a heterologous antimicrobial peptide) and/or a nucleic acid (e.g., a heterologous and/or expressible nucleic acid) comprising a nucleic acid sequence encoding an antimicrobial peptide. A plant and/or plant cell may be a dicot in some embodiments. Examples of a dicot may include, without limitation, coffee, tomato, pepper, tobacco, lima bean, *Arabidopsis*, rubber, orange, grapefruit, lemon, lime, tangerine, mandarin, pummelo, potato, squash, peas, and/or sugar beet. A plant cell may be included in a plant tissue, a plant organ, and/or a whole plant in some embodiments. A plant cell in a tissue, organ, and/or whole plant may be adjacent, according to some embodiments, to one or more isogenic cells and/or one or more heterogenic cells. In some embodiments, a plant may include primary transformants and/or progeny thereof. A plant comprising a nucleic acid (e.g., a heterologous and/or expressible nucleic acid) comprising a nucleic acid sequence encoding an antimicrobial peptide may further comprise an expression control sequence operably linked to the nucleic acid, in some embodiments. A nucleic acid sequence encoding an antimicrobial peptide may be expressed, according to some embodiments, in a plant in one or more up to all (e.g., substantially all) organs, tissues, and/or cell types including, without limitation, stalks, leaves, roots, seeds, flowers, fruit, meristem, parenchyma, storage parenchyma, collenchyma, sclerenchyma, epidermis, mesophyll, bundle sheath, guard cells, protoxylem, metaxylem, phloem, phloem companion, and/or combinations thereof. In some embodiments, a nucleic acid and/or its gene product (e.g., an antimicrobial peptide) may be located in and/or translocated to one or more organelles (e.g., vacuoles, chloroplasts, mitochondria, plastids).

IV. Methods

A. Transforming a Plant

The present disclosure relates, according to some embodiments, to methods for independent transformation of *citrus* (e.g., a native genome of a *citrus* plant). For example, a method may comprise independent transformation, using *Agrobacterium tumefaciens* (At), of the native genome of the orange (*Citrus sinensis*) cultivars "Rohde Red", "Hamlin", and/or "Marrs." A transformation method may comprise contacting a nucleic acid comprising a SoD2 and/or SoD7 sequence (e.g., a SoD2 and/or SoD7 synthetic gene sequence) with a *citrus* plant according to some embodiments. A transformed plant (e.g., a transformed genome of a new orange cultivar) may independently contain, in some embodiments a sequence of a SoD2 gene and/or a SoD7 gene encoding microbial resistance not found within the native gene pool of the *Citrus* genus. According to some embodiments, a transformed orange cultivar plant may comprise a peptide encoded by a SoD2 gene and/or a SoD7 gene. A transformed plant comprising a sequence of a SoD2 gene and/or a SoD7 gene and/or comprising a peptide encoded by a SoD2 gene and/or a SoD7 gene may display resistance to a range (e.g., a broad range) of bacterial and/or fungal pathogens in some embodiments. For example, a transformed plant comprising a sequence of a SoD2 gene and/or a SoD7 gene and/or comprising a peptide encoded by a SoD2 gene and/or a SoD7 gene may display resistance to bacterial canker (*Xanthomonas axonopodis* pv. *citri*) (Xac), and/or *citrus* Huanglongbing (ex greening) caused by *Candidatus Liberibacter asiaticus* (Las). See EXAMPLE section below.

B. Grafting

The present disclosure relates to grafting at least a portion of a first plant (e.g., a *citrus* plant) with at least a portion of a second plant (e.g., a *citrus* plant), according to some embodiments. A first plant may be in any desired condition including, without limitation, a healthy condition, a diseased condition, an injured condition, a stressed condition (e.g., heat, cold, water, and the like), and/or combinations thereof. A first plant may have any desired genotype including, without limitation, wild type, transgenic, mutant, and/or the like with respect to a gene and/or trait of interest.

A second plant may be in any desired condition including, without limitation, a healthy condition, a diseased condition, an injured condition, a stressed condition (e.g., heat, cold, water, and the like), and/or combinations thereof. A second plant may have any desired genotype including, without limitation, wild type, transgenic, mutant, and/or the like with respect to a gene and/or trait of interest. A first and/or a second plant may comprises at least one antimicrobial peptide and/or at least one nucleic acid comprising a sequence encoding at least one antimicrobial peptide. Where both a first plant comprises at least one antimicrobial peptide and/or at least one nucleic acid comprising a sequence encoding at least one antimicrobial peptide and a second plant comprises at least one antimicrobial peptide and/or at least one nucleic acid comprising a sequence encoding at least one antimicrobial peptide, it may be desirable for the first and second plants to have the same and/or different antimicrobial peptides and/or nucleic acids encoding antimicrobial peptides. Grafting may comprise cutting a portion of a first plant to form a fresh cut site, cutting a portion of a second plant to create a second cut site, and/or contacting a first cut site with a second cut site. A cut site may comprise at least one vascular bundle. Grafting may comprise forming a graft junction and/or, optionally, sealing the graft junction (e.g., by coating the periphery of the graft junction with one or more barrier materials).

C. Treating Plant Disease

The present disclosure relates, in some embodiments, to compositions, organisms, systems, and methods for preventing, ameliorating, and/or treating a plant disease (e.g., a *citrus* disease) and/or at least one symptom of a plant disease. For example, a method may comprise grafting at least a portion of a plant (e.g., a *citrus* plant) having a plant disease and/or expressing at least one symptom of a plant disease with at least a portion of a plant (e.g., a *citrus* plant) comprising an antimicrobial peptide. Examples of a plant disease include, without limitation, bacterial canker (*Xanthomonas axonopodis* pv. *citri*) (Xac), and/or *citrus* Huanglongbing (ex greening) caused by *Candidatus Liberibacter asiaticus* (Las). According to some embodiments, preventing, ameliorating, and/or treating a plant disease (e.g., a *citrus* disease) and/or at least one symptom of a plant disease may comprise treating and/or curing one or more devastating bacterial diseases of *citrus*. For example, plants comprising stably integrated SoD2 and SoD7 transgenes in expressible form may display resistance to, without limitation, bacterial canker (*Xanthomonas axonopodis* pv. *citri*) (Xac), and/or *citrus* Huanglongbing (ex greening) caused by *Candidatus Liberibacter asiaticus* (Las). Such resistance has been observed as described in the Examples below.

According to some embodiments, the present disclosure relates to compositions, organisms, systems, and methods for augmenting a plant's native resistance to and/or conferring on a plant resistance to a plant disease (e.g., a *citrus* disease). For example, a method may comprise contacting a plant with an antimicrobial peptide and/or an expressible nucleic acid comprising a nucleic acid sequence encoding an antimicrobial peptide. An expressible nucleic acid comprising a nucleic acid sequence encoding an antimicrobial peptide may be and/or comprise an expression cassette in some embodiments. Contacting may comprise, according to some embodiments, grafting at least a portion of a target plant with a plant comprising an antimicrobial peptide and/or an expressible nucleic acid comprising a nucleic acid sequence encoding an antimicrobial peptide. In some embodiments, contacting may comprise contacting at least a portion of a target plant with a vector (e.g., via *Agrobacterium*-mediated transformation) comprising an antimicrobial peptide and/or an expressible nucleic acid comprising a nucleic acid sequence encoding an antimicrobial peptide. Examples of a plant disease include, without limitation, bacterial canker (*Xanthomonas axonopodis* pv. *citri*) (Xac), and/or *citrus* Huanglongbing (ex greening) caused by *Candidatus Liberibacter asiaticus* (Las).

D. Making a *Citrus*-Expressible Antimicrobial Peptide

In some embodiments, the present disclosure relates to compositions, organisms, systems, and methods for forming a *citrus*-expressible nucleic acid comprising a nucleic acid sequence encoding at least one spinach-derived antimicrobial peptide. For example, a method may comprise identifying an amino acid sequence of an antimicrobial peptide of interest, reverse translating the amino acid sequence to produce a first nucleic acid sequence; codon-optimizing the first nucleic acid sequence for expression in *citrus* to produce a second nucleic acid sequence, and/or synthesizing a nucleic acid having the second nucleic acid sequence. A method may comprise, in some embodiments, covalently bonding a nucleic acid having the second nucleic acid sequence with one or more nucleic acids having expression control sequences that are operable in *citrus* in an operable orientation and/or position relative to the nucleic acid having the second nucleic acid sequence.

As will be understood by those skilled in the art who have the benefit of the instant disclosure, other equivalent or alternative pathogen resistant *citrus* compositions, organisms, systems, and methods can be envisioned without departing from the description contained herein. Accordingly, the manner of carrying out the disclosure as shown and described is to be construed as illustrative only.

Persons skilled in the art may make various changes in the shape, size, number, and/or arrangement of parts without departing from the scope of the instant disclosure. For example, the position and number of expression control sequences, coding sequences, linkers, and/or terminator sequences may be varied. Each disclosed method and method step may be performed in association with any other disclosed method or method step and in any order according to some embodiments. Where the verb "may" appears, it is intended to convey an optional and/or permissive condition, but its use is not intended to suggest any lack of operability unless otherwise indicated. Persons skilled in the art may make various changes in methods of preparing and using a composition, device, and/or system of the disclosure. For example, a composition, device, and/or system may be prepared and or used as appropriate for microbial and/or plant (e.g., with regard to sanitary, infectivity, safety, toxicity, biometric, and other considerations). Where desired, some embodiments of the disclosure may be practiced to the exclusion of other embodiments. For example, some polypeptide embodiments may be practiced to the exclusion of a particular amino acid sequence (e.g., SEQ ID NO:26) and/or some nucleic acid embodiments may be practiced to the exclusion of a particular nucleic acid sequence (e.g., SEQ ID NO:27).

Also, where ranges have been provided, the disclosed endpoints may be treated as exact and/or approximations as desired or demanded by the particular embodiment. Where the endpoints are approximate, the degree of flexibility may vary in proportion to the order of magnitude of the range. For example, on one hand, a range endpoint of about 50 in the context of a range of about 5 to about 50 may include 50.5, but not 52.5 or 55 and, on the other hand, a range endpoint of about 50 in the context of a range of about 0.5 to about 50 may include 55, but not 60 or 75. In addition, it may be desirable, in some embodiments, to mix and match range endpoints. Also, in some embodiments, each figure disclosed (e.g., in one or more of the examples, tables, and/or drawings) may form the basis of a range (e.g., depicted value +/− about 10%, depicted value +/− about 50%, depicted value +/− about 100%) and/or a range endpoint. With respect to the former, a value of 50 depicted in an example, table, and/or drawing may form the basis of a range of, for example, about 45 to about 55, about 25 to about 100, and/or about 0 to about 100.

These equivalents and alternatives along with obvious changes and modifications are intended to be included within the scope of the present disclosure. Accordingly, the foregoing disclosure is intended to be illustrative, but not limiting, of the scope of the disclosure as illustrated by the appended claims.

EXAMPLES

Some specific example embodiments of the disclosure may be illustrated by one or more of the examples provided herein.

Example 1: Plant Material

Plant materials (e.g., *Citrus sinensis*) were generally prepared for transformation as described by Yang et al., *Plant Cell Reports* (2000) 19:1203 et seq.

Example 2: Plasmid Construction and Bacterial Strains

Plasmid construction and bacterial strains were generally performed as described by Yang et al., *Plant Cell Reports* (2000) 19:1203 et seq.

Example 3

*Agrobacterium* Co-Culture and Plant Transformation

*Agrobacterium* co-culture and plant transformation were generally performed as described by Yang et al., *Plant Cell Reports* (2000) 19:1203 et seq.

Example 4: Selection and Regeneration of Transgenic Shoots

Selection and regeneration of transgenic shoots were generally performed as described by Yang et al., *Plant Cell Reports* (2000) 19:1203 et seq.

Example 5: Grafting of Transgenic Shoots

Grafting of transgenic shoots were generally performed as described by Yang et al., *Plant Cell Reports* (2000) 19:1203 et seq.

Example 6: Southern and Northern Analysis

Southern and northern analysis were generally performed as described by Yang et al., *Plant Cell Reports* (2000) 19:1203 et seq.

Example 7: Expression in *Citrus* Trees

Table 1 illustrates specific example embodiments of nucleic acid sequences codon-optimized for *citrus*. Signal peptides and structural gene coding sequences shown are flanked on either side by specific restriction enzyme sites. These sequences were used to construct expression cassettes, vectors, and transformed *Agrobacterium* for preparation of transgenic plants.

TABLE 1

Example embodiments of specific nucleotide sequences of antimicrobial genes. The nucleotide sequences were optimized for codon usage in *Citrus*.

| Antimicrobial Gene | Source of the Optimized Synthetic Gene (code) | Antimicrobial genes specific nucleotide sequences. The 5' nucleotides include the cloning site and a preferred context for the start codon. The 3' nucleotides include the cloning site. |
|---|---|---|
| SoD2 | GenScript (07) | SEQ ID NO: 9 |
|  | CODA (09) | SEQ ID NO: 11 |
| SoD7 | GenScript (08) | SEQ ID NO: 10 |
|  | CODA (10) | SEQ ID NO: 12 |
| SoD2 | DNA 2.0 (11) | SEQ ID NO: 30 |
| SoD7 | DNA 2.0 (12) | SEQ ID NO: 31 |
| SoD2 + SoD7 | GenScript (13) | SEQ ID NOS: 9 and 10 |
| SoD2 + SoD7 no SP | DNA 2.0 (16) | SEQ ID NO: 30 and 31 |

Figure 11:
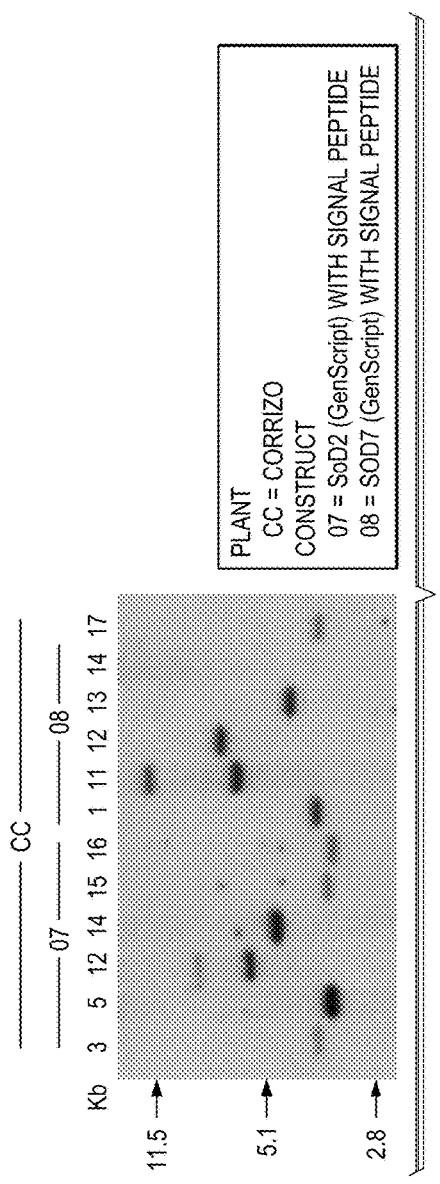
FIG. 11 is a representation of a Southern blot confirming insertion of defensins in Carrizo Citrange (CC) transformed with SoD2 (07) or SoD7 (08) nucleic acids, each comprising a GenScript-optimized sequence for expression in *Citrus*, according to a specific example embodiment of the disclosure.
Figure 12:
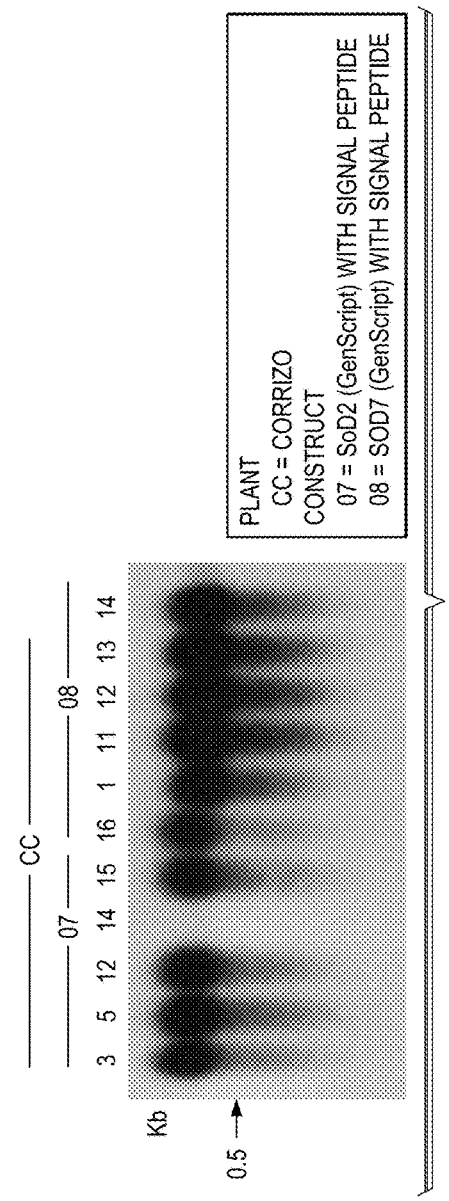
FIG. 12 is a representation of a northern blot showing RNA transcripts among transgenic events in Carrizo Citrange (CC) transformed with SoD2 (07) or SoD7 (08) nucleic acids, each comprising a GenScript-optimized sequence for expression in *Citrus*, according to a specific example embodiment of the disclosure.

The following cultivars were selected for transformation:
Orange: Hamlin ("04"), Rohde Red ("05"), and Marrs ("06") (FIGS. 3-7);
Grapefruit: Ruby Red ("01") (FIGS. 8-11) and Rio Red (Example 14 below);
Carrizo Citrange ("CC") (FIGS. 12-13);
Flying Dragon rootstock ("13" and "16");
Frost Eureka and Frost Lisbon (13" and "16");
Swingle rootstock (13" and "16"); and
C22 rootstock.
Constructs used for each cultivar are shown in Table 2.

TABLE 2

Orange, grapefruit, lemon and citrus rootstock cultivars transformed (seedling epicotyls) with three different synthetic sequences of each SoD2 and SoD7 genes encoding antimicrobial peptides from spinach (*Spinacia oleracea*) (at least 521 events in total).

| Generation | Defensin Synthetic Genes | Synthetic Gene Optimized-Codon Sequence (Sequence Code) | Citrus Cultivars (Cultivar Code) | Transgenic Events Codes (Cultivar and Gene) | Number of Transgenic Events |
|---|---|---|---|---|---|
| 2 (141 events) | SoD2 + SP | GenScript (07) | Hamlin (04) | 0407 | 14 |
|  |  |  | Rohde Red (05) | 0507 | 12 |
|  |  |  | Marrs (06) | 0607 | 6 |
|  |  |  | Carrizo Citrange (CC) | CC2 | 18 |
|  |  | CODA (09) | Hamlin (04) | 0409 | 16 |
|  |  |  | Rohde Red (05) | 0509 | 6 |
|  | SoD7 + SP | GenScript (08) | Hamlin (04) | 0408 | 12 |
|  |  |  | Rohde Red (05) | 0508 | 8 |
|  |  |  | Marrs (06) | 0608 | 7 |
|  |  |  | Carrizo Citrange (CC) | CC7 | 29 |
|  |  | CODA (10) | Hamlin (04) | 0410 | 5 |
|  |  |  | Rohde Red (05) | 0510 | 8 |
| 3 (36 events) | SoD2-no SP | DNA 2.0 (11) | Hamlin (04) | 0411 | 11 |
|  |  |  | Ruby Red (01) | 0111 | 6 |
|  | SoD7-no SP | DNA 2.0 (12) | Hamlin (04) | 0412 | 13 |
|  |  |  | Ruby Red (01) | 0112 | 6 |
| 4 (187 events + 157 Swingle | SoD2 + 7 + SP | GenScript (13) | Hamlin (04) | 413 | 15 |
|  |  |  | Rhode Red (05) | 513 | 14 |
|  |  |  | Rio Red (02) | 213 | 18 |
|  |  |  | Frost Eureka Lemon (10) | 1013 | 30 |
|  |  |  | Frost Lisbon Lemon (11) | 1113 | 33 |
|  |  |  | Swingle Rootstock (12) | 1213 | 157 |
|  |  |  | Flying Dragon Rootstock (09) | 913 | 46 |
|  |  |  | C22 (08) | 813 | 15 |
|  |  |  | Carrizo Citrange (07) | 713 | 16 |

TABLE 2-continued

Orange, grapefruit, lemon and citrus rootstock cultivars transformed (seedling epicotyls) with three different synthetic sequences of each SoD2 and SoD7 genes encoding antimicrobial peptides from spinach (*Spinacia oleracea*) (at least 521 events in total).

| Generation | Defensin Synthetic Genes | Synthetic Gene Optimized-Codon Sequence (Sequence Code) | Citrus Cultivars (Cultivar Code) | Transgenic Events Codes (Cultivar and Gene) | Number of Transgenic Events |
|---|---|---|---|---|---|
| 4 | SoD2 + 7 | GenScript (07 + 08) | Hamlin (04) | 0413 | 15 |
|   |   |   | Rohde Red (05) | 0513 | 1 |
|   |   |   | Rio Red (02) | 0213 | 7 |
|   |   |   | Carrizo Citrange (CC) | CC2 + 7 | 6 |
| 5 | SoD2 + 7-no SP | DNA 2.0 (16) | Hamlin (04) | 416 | Multiple GUS positive plants |
|   |   |   | Frost Eureka Lemon (10) | 1013 | Multiple GUS positive plants |
|   |   |   | Frost Lisbon Lemon (11) | 1113 | Multiple GUS positive plants |
|   |   |   | Rhode Red (05) | 516 | Multiple GUS positive plants |

A. Transformation of Orange

Figure 3:
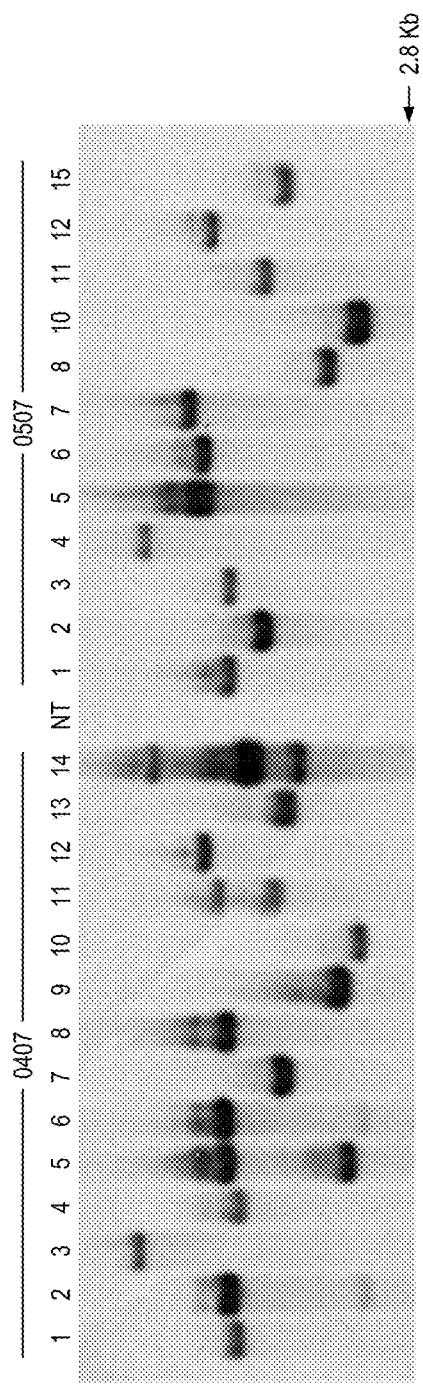
FIG. 3 is a representation of a Southern blot showing insertion number among transgenic events in Hamlin and Rohde Red transformed with a SoD2 (07) nucleic acid comprising a GenScript-optimized sequence for expression in *Citrus*, according to a specific example embodiment of the disclosure.
Figure 4:
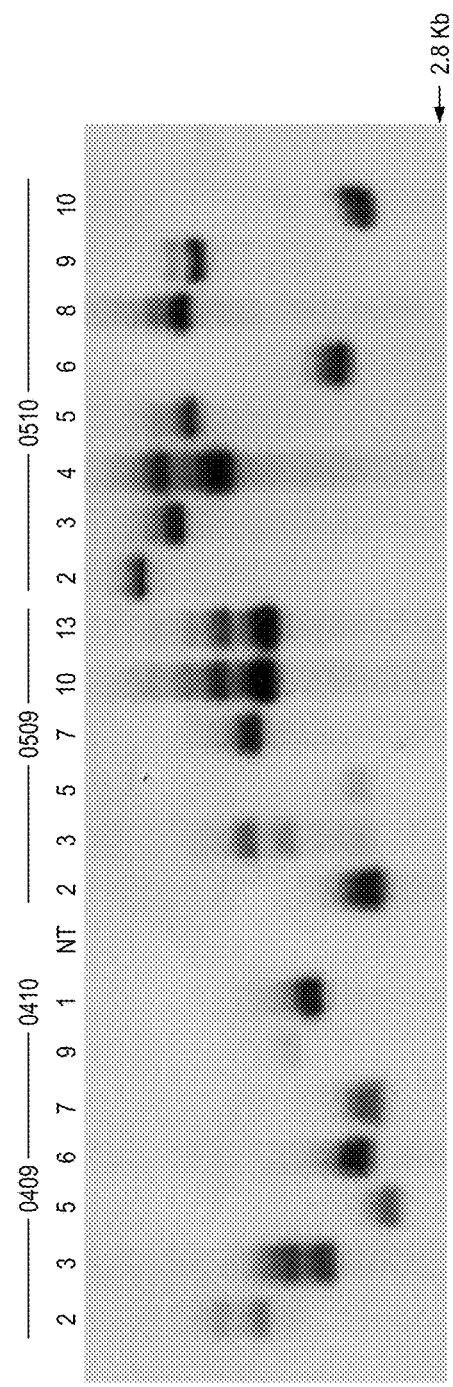
FIG. 4 is a representation of a Southern blot showing insertion number among transgenic events in Hamlin and Rohde Red transformed with SoD2 (09) or SoD7 (10) nucleic acids, each comprising a CODA-optimized sequence for expression in *Citrus*, according to specific example embodiments of the disclosure.

Orange plants were transformed with a single construct comprising GenScript-optimized SoD2 with signal peptide ("07"), GenScript-optimized SoD7 with signal peptide ("08"), CODA-optimized SoD2 with signal peptide ("09"), or CODA-optimized SoD2 with signal peptide ("10"). FIG. 3 is a representation of a Southern blot showing insertion number among transgenic events in Hamlin transformed with GenScript-optimized SoD2 (0407) and Rohde Red transformed with GenScript-optimized SoD2 (0507). FIG. 4 is a representation of a Southern blot showing insertion number among transgenic events in Hamlin transformed with CODA-optimized SoD2 (0409) or CODA-optimized SoD7 (0410) and Rohde Red transformed with CODA-optimized SoD2 (0509) or CODA-optimized SoD7 (0510). Additional transformation events are shown for GenScript-optimized SoD7 ("08") and CODA-optimized SoD2 ("09") in Hamlin in FIG. 9.

Figure 5:
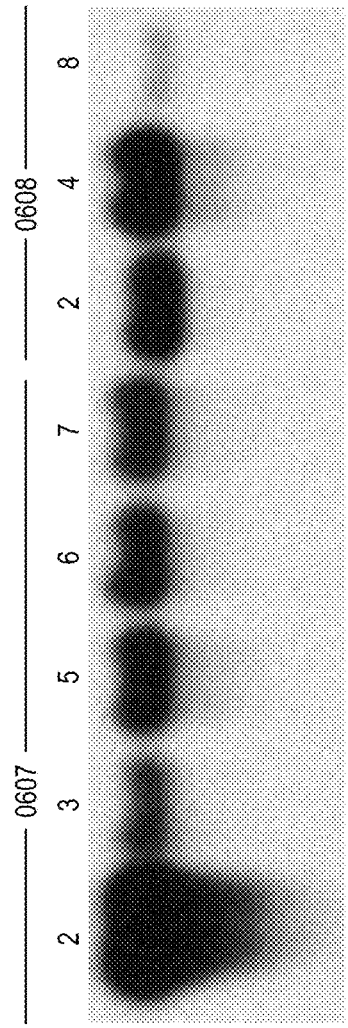
FIG. 5 is a representation of a northern blot showing RNA transcripts among transgenic events in Marrs, transformed with SoD2 (07) or SoD7 (08) nucleic acids, each comprising a GenScript-optimized sequence for expression in *Citrus*, according to a specific example embodiment of the disclosure.
Figure 6:
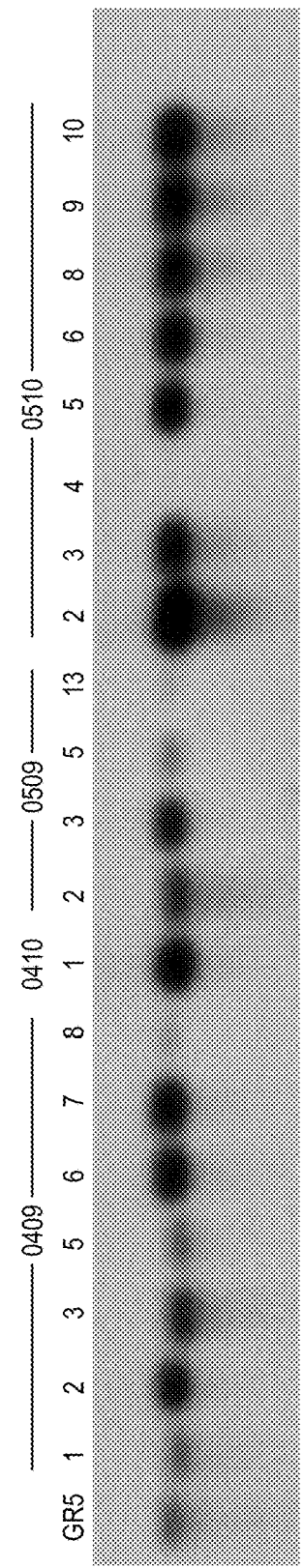
FIG. 6 is a representation of a northern blot showing RNA transcripts among transgenic events in Hamlin and Rohde Red, transformed with SoD2 (09) or SoD7 (10) nucleic acids, each comprising a CODA-optimized sequence for expression in *Citrus*, according to a specific example embodiment of the disclosure.
Figure 7:
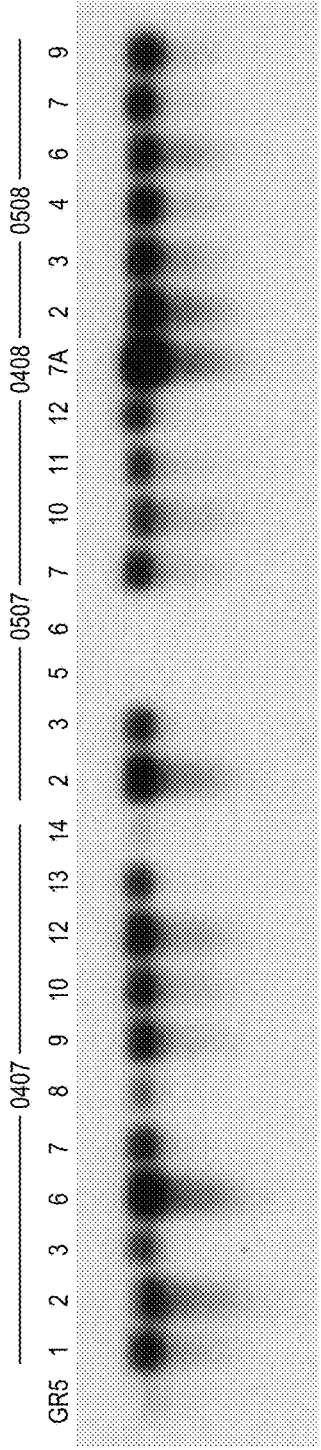
FIG. 7 is a representation of a northern blot showing RNA transcripts among transgenic events in Hamlin and Rohde Red, transformed with SoD2 (07) or SoD7 (08) nucleic acids, each comprising a GenScript-optimized sequence for expression in *Citrus*, according to a specific example embodiment of the disclosure.

Transgenic plants of the orange cultivars Hamlin, Rohde Red, and Marrs (n=82) produce high levels of transcripts of these antimicrobial genes (Table 2 and FIGS. 5-7). FIG. 5 is a representation of a northern blot showing RNA transcripts among transgenic events in Marrs, transformed with genes SoD2 (0607) or SoD7 (0608) GenScript-optimized for codon use in *Citrus*. FIG. 6 is a representation of a northern blot showing RNA transcripts among transgenic events in Hamlin transformed with CODA-optimized SoD2 (0409) or CODA-optimized SoD7 (0410) and Rohde Red transformed with CODA-optimized SoD2 (0509) or CODA-optimized SoD7 (0510). FIG. 7 is a representation of a northern blot showing RNA transcripts among transgenic events in Hamlin transformed with GenScript-optimized SoD2 (0407) or GenScript-optimized SoD7 (0408) and Rohde Red transformed with GenScript-optimized SoD2 (0507) or GenScript-optimized SoD7 (0508). For identification, Table 2 contains the transgenic event codes for cultivar and gene combination.

Figure 8:
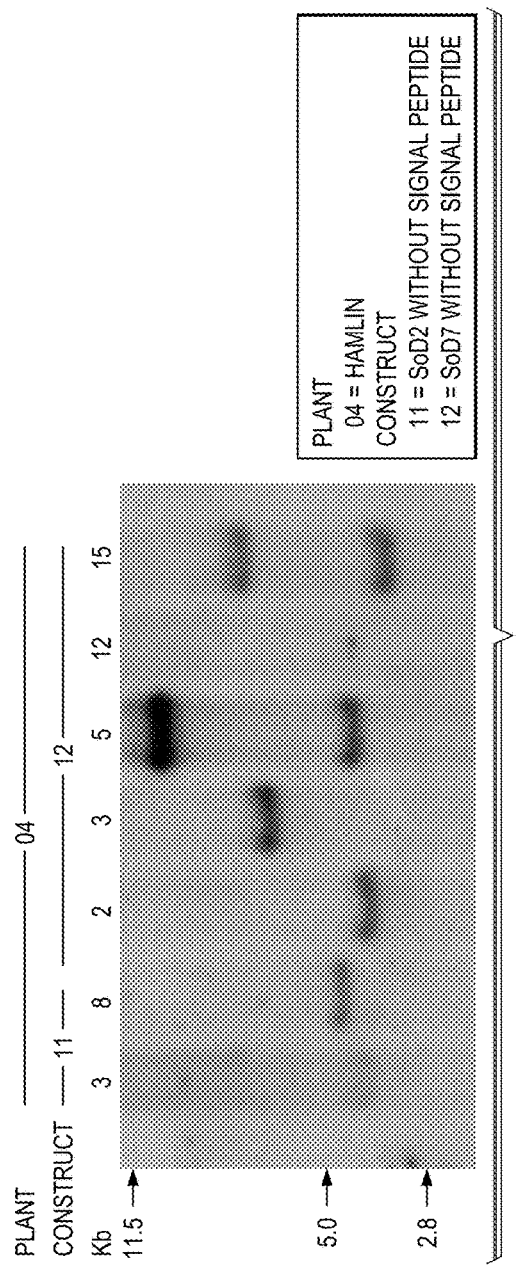
FIG. 8 is a representation of a Southern blot confirming insertion of SoD2 or SoD7 in Hamlin plants, transformed with SoD2 (11) or SoD7 (12) nucleic acids, each comprising a DNA 2.0-optimized sequence for expression in *Citrus*, according to a specific example embodiment of the disclosure.

Orange plants (Hamlin) were also transformed with a single construct comprising DNA 2.0-optimized SoD2 without signal peptide ("11") or DNA 2.0-optimized SoD7 without signal peptide ("12"). FIG. 8 is a representation of a Southern blot confirming insertion of SoD2 or SoD7 in these orange plants. Additional transformation events are shown for SoD7 (12) in Hamlin in FIG. 9.

B. Transformation of Grapefruit

Figure 9:
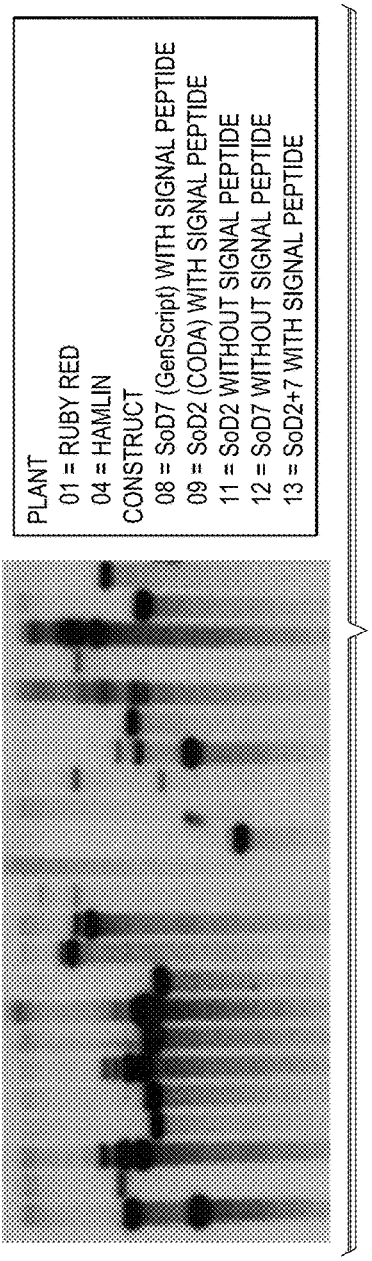
FIG. 9 is a representation of a Southern blot confirming insertion of defensins in Ruby Red (01) or Hamlin (04) transformed with SoD2 (09, 11), SoD7 (08, 12), or both SoD2 and SoD7 (13) nucleic acids, each comprising a sequence optimzed for expression in *Citrus* using a sequence optimization algorithm (GenScript for 08 and 13; Coda for 09, and DNA 2.0 for 11 and 12), according to a specific example embodiment of the disclosure.
Figure 10:
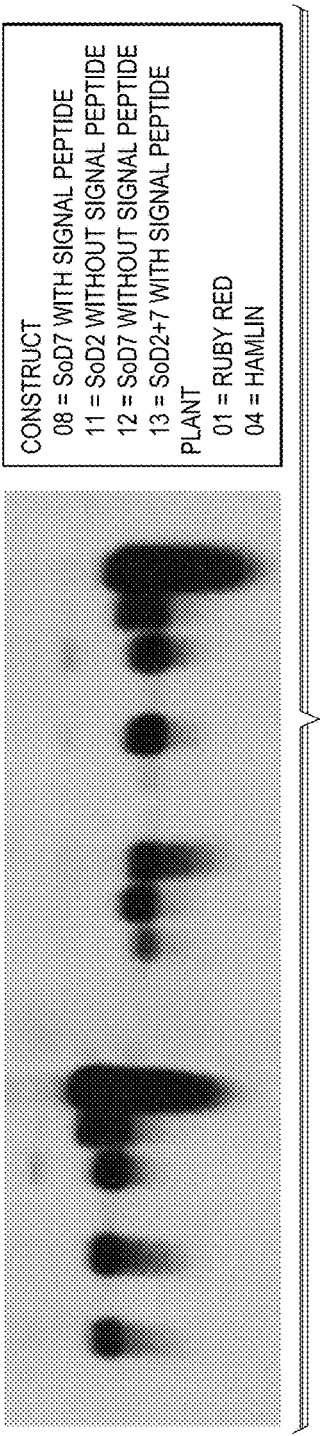
FIG. 10 is a representation of a northern blot showing RNA transcripts among transgenic events in Ruby Red (01) or Hamlin (04), transformed with SoD2 (11), SoD7 (08, 12), or both SoD2 and SoD7 (13) nucleic acids, each comprising a GenScript-optimized sequence (08 and 13) or DNA 2.0-optimized sequence (11 and 12) for expression in *Citrus*, according to a specific example embodiment of the disclosure.

Ruby Red ("01") plants were transformed with a single construct comprising DNA 2.0-optimized SoD2 without signal peptide ("11") or DNA 2.0-optimized SoD7 without signal peptide ("12"). FIG. 9 is a representation of a Southern blot (membrane was exposed to probes for both SoD2 and SoD7) confirming insertion of SoD2 or SoD7 in these grapefruit plants. FIG. 10 is a representation of a northern blot (membrane was exposed to probes for both SoD2 and SoD7) showing RNA transcripts among transgenic events in Ruby Red transformed with SoD2 (0111) or SoD7 (0112). For identification, Table 2 contains the transgenic event codes for cultivar and gene combination.

C. Transformation of Carrizo Citrange and C22

Carrizo Citrange and C22 rootstocks have been transformed with a construct comprising uidA and either SoD2 or SoD7 or SoD2+SoD7. FIG. 11 is a representation of a Southern blot confirming insertion of SoD2 (lanes marked "07") and SoD7 (lanes marked "08") in these Carrizo Citrange plants. FIG. 12 is a representation of a northern blot showing RNA transcripts isolated from these Carrizo Citrange plants (marked "CC") transformed with SoD2 (GenScript-optimized sequence with signal peptide) and SoD7 (GenScript-optimized sequence with signal peptide). For identification, Table 2 contains the transgenic event codes for cultivar and gene combination. A number of C22 transformation events have been confirmed in each by positive GUS staining.

Swingle and Flying Dragon (*citrus* rootstock) plants were transformed with various constructs including a single construct comprising GenScript-optimized SoD2 and SoD7 with signal peptide. Successful transformation of C22, Flying Dragon, and Swingle plants has been at least confirmed by positive GUS staining.

D. Transformation of Lemon

Frost Lisbon and Frost Eureka (lemon) plants were transformed with various constructs including a single construct comprising GenScript-optimized SoD2 and SoD7 with signal peptide. Successful transformation of C22, Flying Dragon, and Swingle plants has been at least confirmed by positive GUS staining.

Example 8: Canker Disease Resistance Assay

Canker disease resistance was assessed using a detached leaf assay generally as described by Francis M I et al., 2010, *Eur J Plant Pathol* 127:571-578. Briefly, detached immature leaves (~75% expanded) were triple rinsed in sterile water to remove debris, sanitized by brief immersion in 70% ethanol followed by 0.5% sodium hypochloride, and again triple rinsed in sterile water. Sanitized leaves (3-4 per replicate×3 replicates) were infiltrated on their abaxial surface with an aqueous suspension of an Xcc strain isolated in Dade County Fla. Innoculated leaves were pressed on the surface of soft water agar plates, parafilm sealed, and incubated in an environmentally-controlled growth chamber.

Figure 13A:
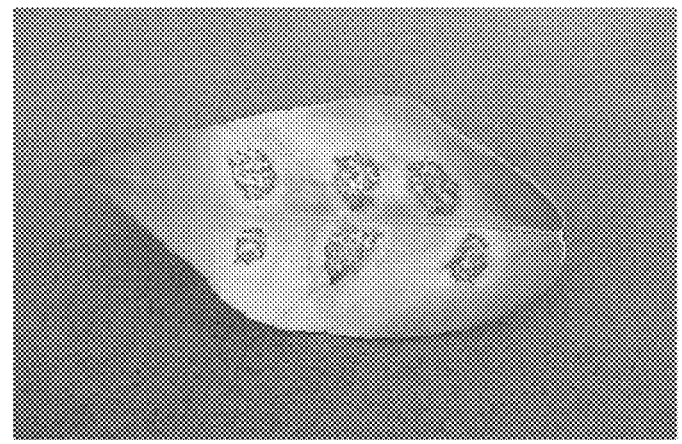
FIG. 13A is a photograph of an excised leaf from a non-transgenic grapefruit tree innoculated with a *citrus* canker pathogen according to specific example embodiments of the disclosure.
Figure 13B:
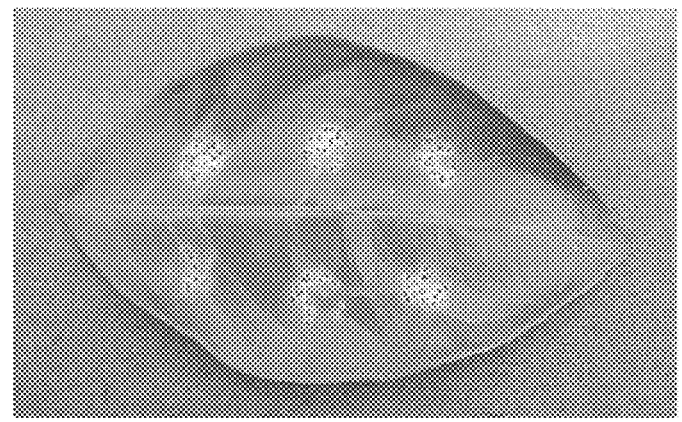
FIG. 13B is a photograph of an excised leaf from an SoD2 transgenic grapefruit tree innoculated with a *citrus* canker pathogen according to specific example embodiments of the disclosure.

FIG. 13A shows the result of inoculating a non-transgenic 'Rio Red' leaf with the *citrus* canker pathogen, as described above, and FIG. 13B shows the result of inoculating a transgenic leaf from a plant of 'Rio Red' expressing SoD2 with the *citrus* canker pathogen, as described above. A large reduction in the size and number of lesion on the transgenic can be seen.

Example 9: *Citrus* Greening (HLB) Disease Resistance Assay by Grafting

Figure 14:
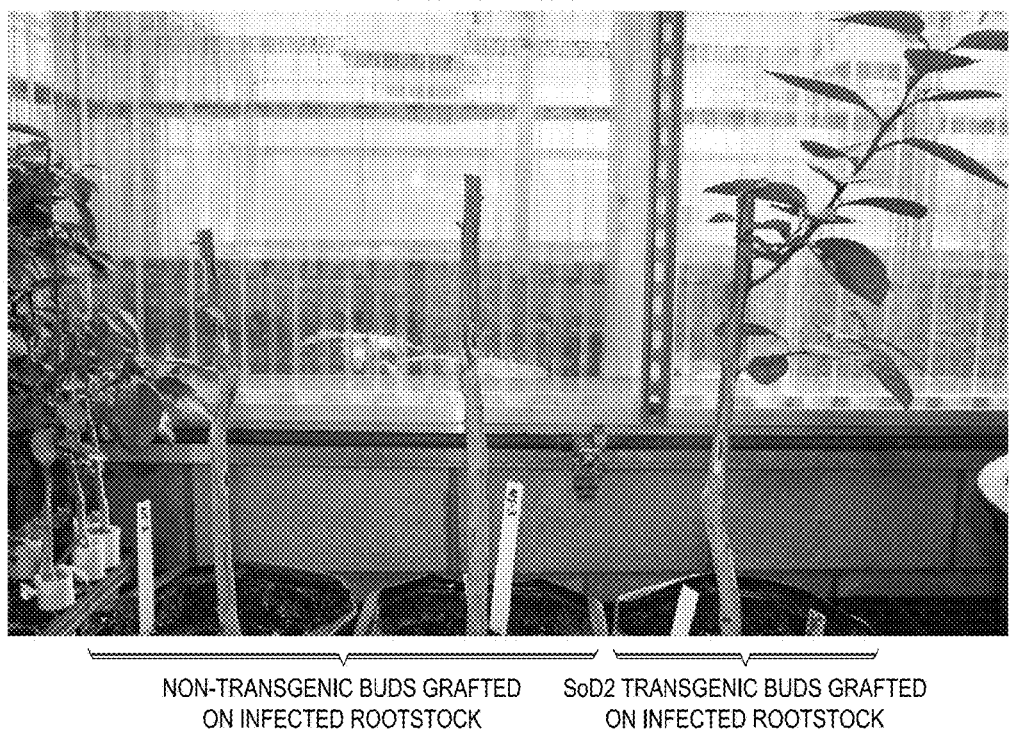
FIG. 14 is a photograph of chimeric grapefruit trees resulting from the graft of uninfected, non-transgenic scions on *citrus* greening infected, non-transgenic rootstocks (left and center) or the graft of uninfected, SoD2 transgenic scions on *citrus* greening infected, non-transgenic rootstock (right), according to specific example embodiments of the disclosure.

FIG. 14 shows the result of graft inoculating non-transgenic 'Rio Red' (two trees on the left) or transgenic 'Rio Red' expressing SoD2 one tree on the right) with the *citrus* greening pathogen. A non-transgenic rootstock (*Cleopatra mandarin*) infected with HLB is used. Onto this rootstock several buds of transgenic 'Rio Red' are grafted and this is replicated. The same protocol is followed for non-transgenic buds of 'Rio Red'. After 8 weeks, vigorous growth can be seen from the transgenic graft, where there is no growth on the controls.

Example 10: *Citrus* Greening (HLB) Disease Resistance Assay by Psyllid Inoculation Resistance to bacterial infection and growth was assessed by two metrics. First, resistance was evaluated by the percentage of infection, namely the number of exposed plants that were infected. Second, a PCR-based method was used to amplify bacterial sequences. In this method, the relative degree of infection influences the number of PCR cycles required to produce detectable signal. For example a heavily infested plant might only require a few cycles while a plant with a low bacterial titer may require more cycles. In general, a plant that requires 30 or more cycles to observe detectable signal is regarded to be uninfected. Since some infections of *citrus* progress slowly, samples were collected for testing at 5 to 11 months after the time of first exposure and thereafter over a period of 6-9 months. The frequency of sample collection may vary from about every 45 days to about every 120 days. Ten to 15 replicates of each transgenic event plus non-transgenic controls are placed haphazardly in an insect proof green house that contains thousands' of psyllids carrying the *citrus* greening pathogen. The first PCR testing is done about five months after continuous exposure to psyllids. DNA extraction and PCR to detect the pathogen is essentially as described by Irey M S et al., 2006, *Proc. Fla. State Hort. Soc.* 119:89-93.

Example 11: Propagation and Resistance of Generation 1

Red Grapefruit (2 varieties) and Sweet Orange (3 varieties) were transformed with *Agrobacterium* comprising an expression vector having an artificial defensin gene construct that included a 2-amino acid insertion in the signal peptide and a single amino acid deletion in the coding sequence (SEQ ID NOS: 26 and 27). A total of 6 transformation events were further tested based on having high levels of SoD2 RNA expressed. Plants were cultivated as described herein and bacterial resistance was assessed as described. A first set of samples were collected after 11 months in the field (D0). Subsequent samples were collected the indicated number of days (42-471) after the first sampling (e.g., D42=11 months+42 days). Results are shown in Table 3.

TABLE 3

Generation 1 Infection Data

| Plant Line | N | 0 | 42 | 90 | 127 | 271 | 384 | 471 |
|---|---|---|---|---|---|---|---|---|
| GR 311 Hamlin | 1 | 0% | 0% | 0% | 0% | 100% | 100% | 100% |
| Non Transgenic Hamlin | 1 | 0% | 0% | 100% | 100% | 100% | 100% | 100% |
| GR 420 Grapefruit | 1 | 0% | 0% | 0% | 0% | 0% | 100% | 100% |
| GR 824 Grapefruit | 2 | 0% | 0% | 50% | 50% | 100% | 100% | 100% |
| GR 867 Grapefruit | 1 | 0% | 0% | 0% | 0% | 100% | 100% | 100% |
| GR 882 Grapefruit | 2 | 0% | 0% | 0% | 50% | 50% | 50% | 50% |
| GR 890 Grapefruit | 1 | 0% | 0% | 0% | 0% | 0% | 100% | 100% |
| Non Transgenic Grapefruit | 7 | 0% | 0% | 0% | 14% | 0% | 57% | 57% |
| Non Transgenic Grapefruit Border | 6 | 0% | 0% | 0% | 0% | 50% | 50% | 50% |
| Total | 22 | 0% | 0% | 9% | 18% | 41% | 68% | 68% |

Example 12: Propagation and Resistance of Generation 2

Sweet Orange (2 varieties) were transformed with *Agrobacterium* comprising one of the following defensin gene constructs:
(a) GenScript-optimized SoD2 with tobacco PR-1b signal peptide (SEQ ID NO: 9),
(b) CODA-optimized SoD2 with tobacco PR-1b signal peptide (SEQ ID NO: 11),
(c) GenScript-optimized SoD7 with tobacco PR-1b signal peptide (SEQ ID NO: 10), or
(d) CODA-optimized SoD7 with tobacco PR-1b signal peptide (SEQ ID NO: 12).

A total of 71 transformation events were observed. Plants were cultivated as described herein and bacterial resistance was assessed as described. A first set of samples were collected after 5 months in the psyllid house (Day 0). Subsequent samples were collected the indicated number of days after the first sampling (e.g., Day 73=5 months+73 days). Results are shown in FIG. 15, FIG. 16, Table 4, and Table 5.

TABLE 4

| | | | | | Generation 2 Infection Data | | | | | | | |
|---|---|---|---|---|---|---|---|---|---|---|---|---|
| | | | | | 1st Sampling | | 2nd Sampling | | 3rd Sampling | | Partial 4th Sampling | |
| Code | Scion[1] | Genotype[2] | Rootstock[3] | Gene[4] | Day 0 | Mean Ct | Day 73 | Mean Ct | Day 170 | Mean Ct | Day 317 | Mean Ct |
| 0407-01 | H | SO | Cm | SoD2 (G) | 13% | 23.02 | 33% | 26.09 | 33% | 23.28 | | |
| 0407-02 | H | SO | Cm | SoD2 (G) | 0% | | 27% | 28.78 | 47% | 26.55 | | |
| 0407-03 | H | SO | Cm | SoD2 (G) | 0% | | 7% | 24.84 | 33% | 29.32 | | |
| 0407-04 | H | SO | Cm | SoD2 (G) | 20% | 25.56 | 27% | 27.18 | 40% | 25.28 | | |
| 0407-06 | H | SO | Cm | SoD2 (G) | 7% | 31.07 | 7% | 26.16 | 13% | 22.52 | 67% | 28.81 |
| 0407-07 | H | SO | Cm | SoD2 (G) | 20% | 27.37 | 13% | 25.96 | 27% | 25.85 | 80% | 27.26 |
| 0407-09 | H | SO | Cm | SoD2 (G) | 13% | 26.05 | 27% | 26.83 | 33% | 22.90 | | |
| 0407-10 | H | SO | Cm | SoD2 (G) | 7% | 23.57 | 27% | 26.04 | 47% | 25.32 | | |
| 0407-11 | H | SO | Cm | SoD2 (G) | 7% | 26.75 | 33% | 26.21 | 67% | 24.87 | | |
| 0407-12 | H | SO | Cm | SoD2 (G) | 7% | 31.66 | 13% | 24.51 | 33% | 23.39 | | |
| 0407-13 | H | SO | Cm | SoD2 (G) | 13% | 23.52 | 27% | 27.89 | 40% | 23.54 | | |
| 0408-01 | H | SO | Cm | SoD7 (G) | 13% | 24.88 | 27% | 25.55 | 53% | 26.15 | | |
| 0408-07A | H | SO | Cm | SoD7 (G) | 7% | 23.40 | 20% | 28.48 | 27% | 22.64 | 80% | 27.08 |
| Hamlin NT Control | H | SO | Cm | Control | 0% | | 20% | 28.83 | 40% | 24.59 | 87% | 25.92 |
| 0409-02 | H | SO | Cm | SoD2 (C) | 7% | 27.34 | 0% | | 20% | 24.04 | 80% | 26.23 |
| 0409-03 | H | SO | Cm | SoD2 (C) | 7% | 22.28 | 7% | 28.79 | 27% | 22.12 | 93% | 25.52 |
| 0409-06 | H | SO | Cm | SoD2 (C) | 0% | | 20% | 26.52 | 40% | 24.01 | | |
| 0409-07 | H | SO | Cm | SoD2 (C) | 0% | | 20% | 26.31 | 40% | 23.17 | | |
| 0410-01 | H | SO | Cm | SoD7 (C) | 0% | | 40% | 22.96 | 73% | 24.78 | | |
| 0507-01 | RR | SO | Cm | SoD2 (G) | 0% | | 47% | 26.35 | 60% | 23.60 | | |
| 0507-02 | RR | SO | Cm | SoD2 (G) | 13% | 28.26 | 40% | 22.18 | 47% | 25.14 | | |
| 0507-03 | RR | SO | Cm | SoD2 (G) | 13% | 24.61 | 47% | 26.64 | 60% | 23.59 | | |
| 0507-04 | RR | SO | Cm | SoD2 (G) | 13% | 26.21 | 27% | 25.25 | 40% | 24.63 | | |
| 0507-07 | RR | SO | Cm | SoD2 (G) | 0% | | 13% | 27.42 | 27% | 22.61 | 67% | 29.19 |
| 0507-08 | RR | SO | Cm | SoD2 (G) | 7% | 25.97 | 40% | 26.37 | 40% | 24.03 | | |
| 0507-10 | RR | SO | Cm | SoD2 (G) | 7% | 26.04 | 27% | 25.71 | 40% | 25.29 | | |
| 0507-11 | RR | SO | Cm | SoD2 (G) | 0% | | 40% | 26.51 | 53% | 22.26 | | |
| 0507-12 | RR | SO | Cm | SoD2 (G) | 0% | | 20% | 17.61 | 13% | 22.56 | 77% | 27.17 |
| 0507-15 | RR | SO | Cm | SoD2 (G) | 13% | 24.49 | 53% | 25.65 | 73% | 23.10 | | |
| 0508-02 | RR | SO | Cm | SoD7 (G) | 13% | 29.40 | 47% | 26.25 | 73% | 23.90 | | |
| 0508-03 | RR | SO | Cm | SoD7 (G) | 7% | 31.44 | 33% | 24.53 | 60% | 25.43 | | |
| 0508-04 | RR | SO | Cm | SoD7 (G) | 13% | 25.65 | 20% | 28.00 | 60% | 25.74 | | |
| 0508-06 | RR | SO | Cm | SoD7 (G) | 0% | | 7% | 27.72 | 27% | 24.33 | 79% | 25.56 |
| 0508-07 | RR | SO | Cm | SoD7 (G) | 27% | 26.86 | 67% | 25.30 | 100% | 24.76 | 100% | 21.87 |
| 0508-08 | RR | SO | Cm | SoD7 (G) | 7% | 24.35 | 27% | 24.55 | 53% | 23.07 | | |
| 0508-09 | RR | SO | Cm | SoD7 (G) | 20% | 25.55 | 33% | 24.69 | 60% | 24.40 | | |
| 0508-10 | RR | SO | Cm | SoD7 (G) | 7% | 25.96 | 33% | 25.94 | 47% | 23.30 | | |
| Rohde Red NT Control | RR | SO | Cm | Control | 13% | 27.03 | 27% | 25.64 | 67% | 25.46 | 100% | 22.32 |
| 0509-02 | RR | SO | Cm | SoD2 (C) | 13% | 24.36 | 53% | 23.07 | 60% | 23.77 | | |
| 0509-03 | RR | SO | Cm | SoD2 (C) | 13% | 25.28 | 27% | 26.60 | 53% | 26.02 | | |
| 0509-07 | RR | SO | Cm | SoD2 (C) | 7% | 30.19 | 20% | 24.85 | 47% | 25.71 | | |
| 0509-10 | RR | SO | Cm | SoD2 (C) | 20% | 27.29 | 20% | 24.93 | 67% | 26.26 | | |
| 0510-02 | RR | SO | Cm | SoD7 (C) | 7% | 30.66 | 27% | 23.36 | 47% | 24.42 | | |
| 0510-03 | RR | SO | Cm | SoD7 (C) | 7% | 22.01 | 20% | 24.70 | 53% | 25.39 | | |
| 0510-05 | RR | SO | Cm | SoD7 (C) | 7% | 31.54 | 7% | 31.03 | 7% | 31.22 | 17% | 35.78 |
| 0510-06 | RR | SO | Cm | SoD7 (C) | 0% | | 33% | 26.56 | 80% | 24.48 | 93% | 23.67 |
| 0510-08 | RR | SO | Cm | SoD7 (C) | 7% | 23.07 | 47% | 25.29 | 60% | 22.32 | | |
| 0510-09 | RR | SO | Cm | SoD7 (C) | 0% | | 33% | 24.63 | 47% | 24.02 | | |
| 0510-10 | RR | SO | Cm | SoD7 (C) | 0% | | 20% | 27.68 | 60% | 25.16 | | |
| Extra NT Controls | | | | | | | | | | | | |
| Hamlin | H | SO | Cm | Control | 0% | | 40% | 27.29 | 47% | 23.25 | | |
| Hamlin | H | SO | Cm | Control | 7% | 24.49 | 13% | 24.87 | 33% | 25.58 | | |
| Hamlin | H | SO | Cm | Control | 0% | | 33% | 24.44 | 33% | 25.82 | | |
| Rohde Red | RR | SO | Cm | Control | 7% | 24.61 | 33% | 26.27 | 27% | 22.98 | | |
| Rohde Red | RR | SO | Cm | Control | 0% | | 40% | 27.07 | 33% | 24.49 | | |
| Rohde Red | RR | SO | Cm | Control | 7% | 24.36 | 33% | 29.01 | 47% | 26.50 | | |

[1] H = Hamlin; RR = Rohde Red
[2] SO = Sweet Orange
[3] Cm = Cleopatra mandarin
[4] (G) = GenScript-optimized sequence; (C) = CODA-optimized sequence Example 13: Propagation and Resistance of Generation 3

One Sweet Orange variety and one grapefruit variety were transformed with *Agrobacterium* comprising one of the following defensin gene constructs:

(a) GenScript-optimized SoD2 with no signal peptide (SEQ ID NO: 3), or (b) GenScript-optimized SoD7 with no signal peptide (SEQ ID NO: 4).

A total of 36 transformation events were observed. Plants were cultivated as described herein and bacterial resistance was assessed as described. A first set of samples were collected after 5 months in the psyllid house (Day 0). Subsequent samples were collected the indicated number of days after the first sampling (e.g., Day 103=5 months+103 days). Results are shown in FIG. 16 and Table 5.

TABLE 5

Generations 2 and 3 Infection Data

| | | | | | 1st Sampling | 2nd Sampling | | | 3rd Sampling | | |
|---|---|---|---|---|---|---|---|---|---|---|---|
| Code | Scion[1] | Genotype[2] | Rootstock[3] | Gene[4] | Day 0 | Day 103 | Avg Ct | Ct of Positive | Day 215 | Avg Ct | Ct of Positive |
| 41103 | H | SO | Cm | SoD2 (-P) | 10% | 10% | 37.98 | 24.78 | 10% | 36.83 | 19.62 |
| 41108 | H | SO | Cm | SoD2 (-P) | 0% | 0% | 40.00 | | 0% | 38.93 | |
| 41107 | H | SO | Cm | SoD2 (-P) | 10% | 14% | 37.24 | 23.44 | 14% | 35.28 | 21.02 |
| 41110 | H | SO | Cm | SoD2 (-P) | 0% | 10% | 38.18 | 26.35 | 20% | 35.24 | 23.33 |
| 40918 | H | SO | Cm | SoD2 (C) | 0% | 0% | 39.74 | | 10% | 36.97 | 21.53 |
| 40915 | H | SO | Cm | SoD2 (C) | 0% | 11% | 38.07 | 25.22 | 22% | 34.31 | 24.44 |
| 41004 | H | SO | Cm | SoD7 (C) | 0% | 10% | 38.37 | 23.72 | 20% | 35.24 | 25.54 |
| 40814 | H | SO | Cm | SoD7 (G) | 0% | 20% | 36.62 | 26.39 | 10% | 36.85 | 24.35 |
| 40817 | H | SO | Cm | SoD7 (G) | 10% | 10% | 37.97 | 22.93 | 30% | 34.17 | 23.40 |
| 11206 | RR | Gf | Cm | SoD7 (-P) | 0% | 30% | 35.18 | 23.93 | 40% | 32.27 | 24.69 |
| 11204 | RR | Gf | Cm | SoD7 (-P) | 0% | 10% | 37.63 | 24.56 | 30% | 33.49 | 22.16 |
| 40813 | H | SO | Cm | SoD7 (G) | 10% | 11% | 37.73 | 22.63 | 44% | 31.96 | 22.62 |
| 11201 | RR | Gf | Cm | SoD7 (-P) | 0% | 30% | 35.87 | 26.76 | 30% | 33.71 | 23.06 |
| 41109 | H | SO | Cm | SoD2 (-P) | 0% | 10% | 38.46 | 24.64 | 10% | 37.25 | 22.14 |
| 11208 | RR | Gf | Cm | SoD7 (-P) | 0% | 0% | 39.82 | | 0% | 38.42 | |
| 11108 | RR | Gf | Cm | SoD2 (-P) | 0% | 0% | 38.60 | | 13% | 36.15 | 21.66 |
| 11103 | RR | Gf | Cm | SoD2 (-P) | 0% | 20% | 36.98 | 26.00 | 20% | 33.73 | 19.99 |
| 60811 | M | SO | Cm | SoD7 (G) | 0% | 0% | 39.66 | | 0% | 39.03 | |
| Marrs WT | M | SO | Cm | Control | 0% | 10% | 38.81 | 28.14 | 20% | 35.57 | 24.93 |
| 40820 | H | SO | Cm | SoD7 (G) | 10% | 20% | 36.99 | 25.96 | 30% | 34.94 | 23.65 |
| 41101 | H | SO | Cm | SoD2 (-P) | 0% | 10% | 37.65 | 23.09 | 20% | 34.53 | 21.92 |
| Ruby Red WT | RR | Gf | Cm | Control | 0% | 0% | 39.39 | | 30% | 34.88 | 26.93 |
| 11105 | RR | Gf | Cm | SoD2 (-P) | 0% | 10% | 38.64 | 26.38 | 20% | 36.32 | 24.70 |
| 40810 A | H | SO | Cm | SoD7 (G) | 0% | 25% | 35.46 | 24.94 | 50% | 30.83 | 23.08 |
| 11203 | RR | Gf | Cm | SoD7 (-P) | 0% | 20% | 37.84 | 29.19 | 20% | 35.55 | 21.51 |
| 40914 | H | SO | Cm | SoD2 (C) | 0% | 0% | 39.66 | | 30% | 35.22 | 26.78 |
| 40812 | H | SO | Cm | SoD7 (G) | 0% | 10% | 37.99 | 27.44 | 20% | 35.67 | 21.75 |
| 41102 | H | SO | Cm | SoD2 (-P) | 10% | 40% | 35.03 | 27.58 | 60% | 29.83 | 23.83 |
| Hamlin WT | H | SO | Cm | Control | 0% | 40% | 33.76 | 24.41 | 50% | 29.52 | 22.14 |
| 60813 | M | SO | Cm | SoD7 (G) | 0% | 0% | 40.00 | | 13% | 37.06 | 24.02 |
| 60804 | M | SO | Cm | SoD7 (G) | 10% | 0% | 39.80 | | 0% | 37.74 | |
| 60703 | M | SO | Cm | SoD2 (G) | 0% | 33% | 36.35 | 30.88 | 33% | 36.07 | 25.07 |
| 60802 | M | SO | Cm | SoD7 (G) | 0% | 0% | 39.18 | | 10% | 37.87 | 31.23 |
| 60702 | M | SO | Cm | SoD2 (G) | 0% | 10% | 38.30 | 27.16 | 20% | 35.46 | 24.11 |
| 41211 | H | SO | Cm | SoD7 (-P) | 10% | 20% | 36.47 | 24.33 | 30% | 34.02 | 21.20 |
| 41203 | H | SO | Cm | SoD7 (-P) | 0% | 0% | 39.93 | | 0% | 38.17 | |
| 60812 | M | SO | Cm | SoD7 (G) | 0% | 0% | 40.00 | | 10% | 36.79 | 23.40 |
| 60810 | M | SO | Cm | SoD7 (G) | 10% | 20% | 37.25 | 26.25 | 70% | 27.87 | 23.44 |
| 60707 | M | SO | Cm | SoD2 (G) | 0% | 10% | 38.51 | 25.13 | 40% | 33.77 | 25.40 |
| 60701 | M | SO | Cm | SoD2 (G) | 0% | 20% | 37.45 | 28.07 | 50% | 30.37 | 23.85 |
| 41210 | H | SO | Cm | SoD7 (-P) | 0% | 0% | 39.60 | | 20% | 34.62 | 22.91 |
| 41202 | H | SO | Cm | SoD7 (-P) | 10% | 17% | 35.89 | 23.81 | 50% | 30.85 | 22.69 |
| 60706 | M | SO | Cm | SoD2 (G) | 0% | 10% | 37.64 | 25.23 | 50% | 30.82 | 23.24 |
| 41209 | H | SO | Cm | SoD7 (-P) | 0% | 40% | 33.36 | 24.97 | 70% | 27.11 | 22.03 |
| 41113 | H | SO | Cm | SoD2 (-P) | 20% | 60% | 31.02 | 25.03 | 80% | 25.36 | 21.70 |
| 41215 | H | SO | Cm | SoD7 (-P) | 20% | 40% | 33.73 | 24.32 | 70% | 25.95 | 21.94 |
| 60808 | M | SO | Cm | SoD7 (G) | 0% | 0% | 39.35 | | 22% | 36.32 | 22.11 |
| 41208 | H | SO | Cm | SoD7 (-P) | 0% | 0% | 39.62 | | 11% | 37.30 | 22.04 |
| 41112 | H | SO | Cm | SoD2 (-P) | 20% | 20% | 35.94 | 25.32 | 40% | 31.22 | 22.22 |
| 41214 | H | SO | Cm | SoD7 (-P) | 0% | 20% | 36.57 | 24.47 | 50% | 29.72 | 21.99 |
| 60705 | M | SO | Cm | SoD2 (G) | 0% | 10% | 37.96 | 23.82 | 10% | 36.57 | 21.02 |
| 41204 | H | SO | Cm | SoD7 (-P) | 0% | 0% | 40.00 | | 10% | 36.50 | 22.28 |
| 41111 | H | SO | Cm | SoD2 (-P) | 10% | 13% | 37.98 | 23.82 | 25% | 35.18 | 24.46 |
| Hamlin WT | H | SO | Cm | Control | 0% | 25% | 35.56 | 26.41 | 55% | 29.82 | 22.51 |

TABLE 5-continued

Generations 2 and 3 Infection Data

| | | | | | 1st Sampling | 2nd Sampling | | | 3rd Sampling | | |
|---|---|---|---|---|---|---|---|---|---|---|---|
| Code | Scion[1] | Genotype[2] | Rootstock[3] | Gene[4] | Day 0 | Day 103 | Avg Ct | Ct of Positive | Day 215 | Avg Ct | Ct of Positive |
| Marrs WT | M | SO | Cm | Control | 0% | 0% | 39.16 | | 33% | 33.11 | 22.73 |

[1]H = Hamlin; RR = Ruby Red; M = Marrs
[2]SO = Sweet Orange; Gf = Grapefruit
[3]Cm = Cleopatra mandarin
[4](G) = GenScript-optimized sequence; (C) = CODA-optimized sequence; (-P) = DNA 2.0-optimized sequence with no signal peptide Example 14: Propagation and Resistance of Generation 4

A first line of Sweet Orange (2 varieties), one grapefruit, and two rootstocks were prepared to co-express (i) GenScript SoD2 with tobacco PR-1b signal peptide (SEQ ID NO: 9) and (ii) GenScript SoD7 with tobacco PR-1b signal peptide (SEQ ID NO: 10). More specifically, plants were transformed with a double defensin construct comprising, in a 5' to 3' direction SoD2, uidA, and SoD7 (13). A total of 29 transformation events were observed with another 28 GUS-positive candidates in tissue culture or just out of tissue culture. Plants confirmed to co-express SoD2 and SoD7 will be cultivated and evaluated in infection assays to determine the degree to which coexpression prevents, ameliorates, and/or treats infection.

FIG. 9 is a representation of a Southern blot (membrane was exposed to probes for both SoD2 and SoD7) showing insertion number among transgenic events in Hamlin transformed with a double defensin construct comprising SoD2 and SoD7 (0413). FIG. 10 also shows insertion number among transgenic events in Hamlin transformed with a double defensin construct comprising SoD2 and SoD7 (0413).

Figure 17:
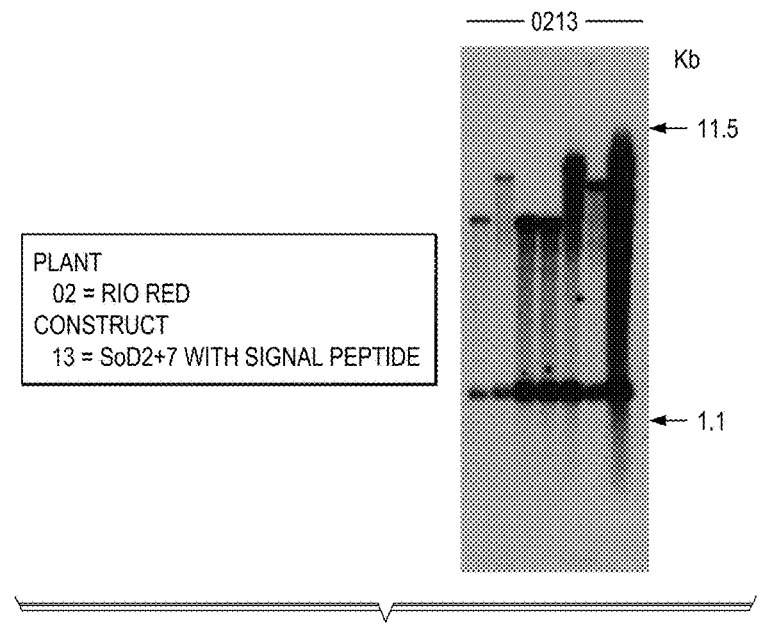
FIG. 17 is a representation of a Southern blot confirming insertion of defensins in Rio Red (01) transformed with both SoD2 and SoD7 (13) nucleic acids, each comprising a GenScript-optimized sequence for expression in *Citrus*, according to a specific example embodiment of the disclosure.
Figure 18:
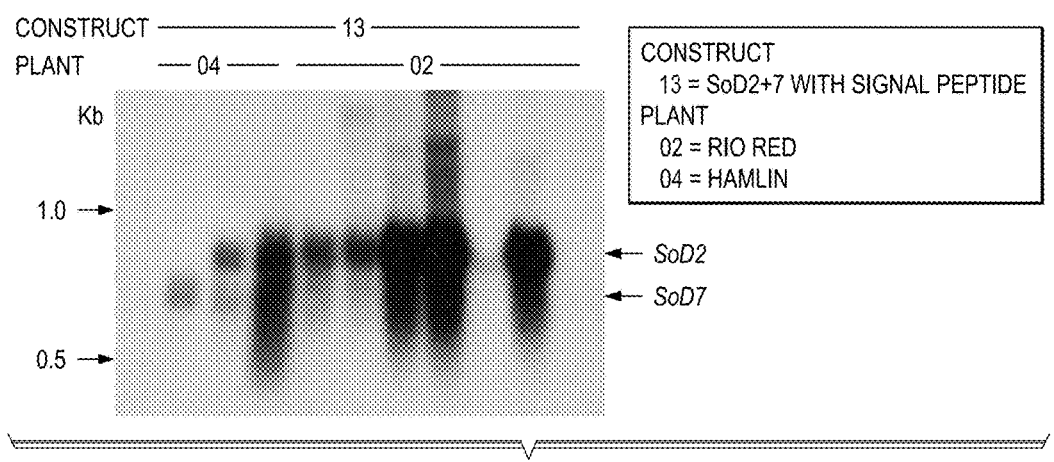
FIG. 18 is a representation of a northern blot showing RNA transcripts among transgenic events in Rio Red (01) or Hamlin (04), transformed with both SoD2 and SoD7 (13) nucleic acids, each comprising a GenScript-optimized sequence for expression in *Citrus*, according to a specific example embodiment of the disclosure.

Rio Red plants (02) were transformed with a double defensin construct (13). FIG. 17 is a representation of a Southern blot confirming insertion of both SoD2 and SoD7 in these Rio Red plants. DNA was cut with a single restriction enzyme that cut within SoD2, uidA, and SoD7 and blotted with both SoD2 and SoD7 probes simultaneously. FIG. 18 is a representation of a northern blot showing RNA transcripts isolated from Rio Red plants (marked "02") transformed with SoD2 (GenScript-optimized sequence with signal peptide) and SoD7 (GenScript-optimized sequence with signal peptide). RNA transcripts isolated from Hamlin plants (marked "04") are also shown.

Example 15: Propagation and Resistance of Generation 5

Evaluation of coexpression of SoD2 and SoD7 is underway. A line of Sweet Orange (1 variety) was prepared to co-express (i) DNA 2.0 SoD2 with no signal peptide (SEQ ID NO: 30) and (ii) DNA 2.0 SoD7 with no signal peptide (SEQ ID NO: 31). Transformation and expression may be confirmed by Southern and northern blotting analysis. Plants may be cultivated as described herein and bacterial resistance evaluated as described. Plants confirmed to co-express SoD2 and SoD7 may be cultivated and evaluated in infection assays to determine the degree to which coexpression prevents, ameliorates, and/or treats infection.

Example 16: Expression of Defensin Constructs in Various Plants

Stable expression of defensin constructs comprising nucleic acid sequences condon-optimized for *citrus* has been confirmed in the following:

| Cultivar | Gene Code | # Events |
|---|---|---|
| Rio Red Grapefruit | 13 | 18 |
| Ruby Red Grapefruit | 11 and 12 | 12 |
| Hamlin Sweet Orange | 07, 08, 09, 10, 11, 12, 13, and 16 | over 86 |
| Marrs Sweet Orange | 07 and 08 | 13 |
| Rohde Red Valencia Orange | 07, 08, 09, 10, 13 | over 48 |
| Frost Eureka Lemon | 13 and 16 | over 30 |
| Frost Lisbon Lemon | 13 and 16 | over 33 |
| C22 and Carrizo Citrange Rootstocks | 07, 08, 13 | 42 |
| Flying dragon and Swingle Rootstocks | 13 | Multiple GUS+ |

For all constructs, individual transformation events have been found spanning a range of expression levels from no expression (e.g., since Southern results demonstrate the gene is present, often in multiple copies, it may be that the transgene has been silenced) to low expression to high expression.

Example 17: Antibodies to SoD2 and SoD7

Figure 19:
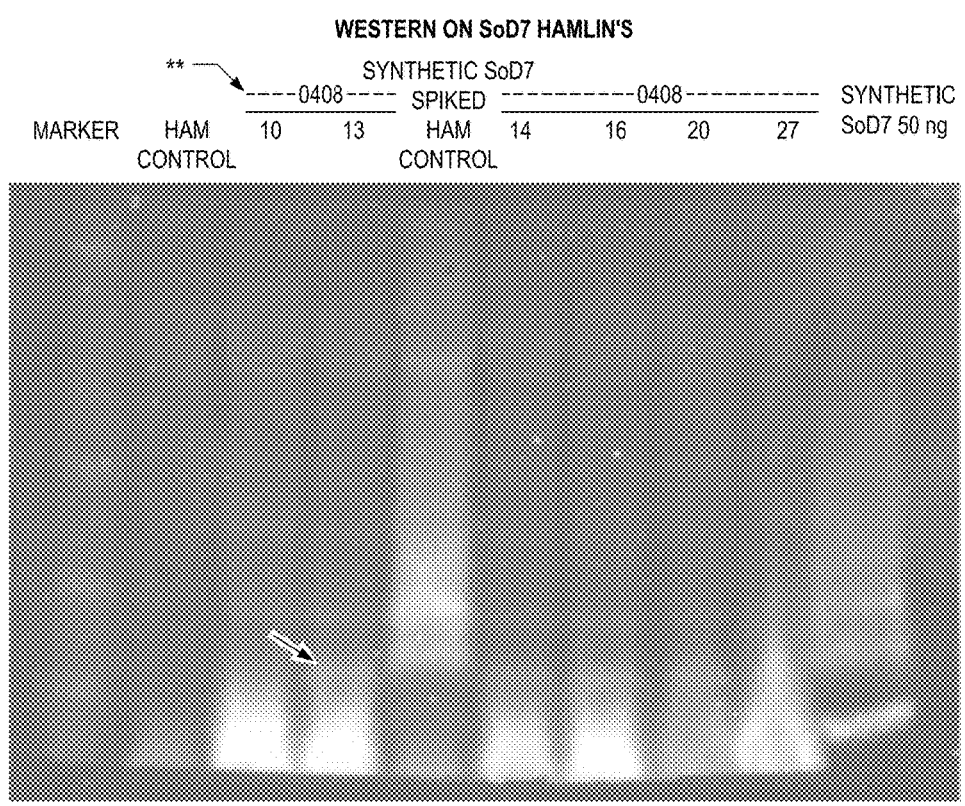
FIG. 19 is a Western blot illustrating binding of an anti-SoD7 according to specific example embodiments of the disclosure to samples containing SoD7.

Antibodies were raised to SoD2 and SoD7. Full length SoD7 peptide was synthesized by GenScript. Aliquots of synthetic SoD7 (200 ug each time) were injected into each of 2 different rabbits every three weeks for a total of 4 injections. Sera was collected 2 weeks after the third 2 weeks after the fourth injections. IgG was purified using a Protein A column. SoD7 specific IgG was purified by passing the IgG preparation over a column of synthetic SoD7 conjugated to agarose beads and then eluting with a low pH buffer Eluate was screened for binding to a dilution series from 1 ng to 100 ng synthetic SoD7. FIG. 19 is a Western blot illustrating binding of the purified SoD7-specific IgG antibodies to about 20 ng of SoD7 peptide in either transgenic plants (lanes 3, 4, and 6-9), non-transgenic plants spiked with synthetic SoD7 peptide (lane 5), or pure synthetic SoD7 (lane 10).

What is claimed is:

1. A method for grafting a first *citrus* plant to a second *citrus* plant, the method comprising:
    contacting a scion of the first plant with a rootstock of the second plant,
        wherein the first plant or the second plant comprises an expression cassette, the expression cassette comprising, in a 5' to 3' direction:
            an expression control sequence,
            a spinach defensin nucleic acid operably linked to the expression control sequence,
            wherein the nucleic acid sequence of the spinach defensin is at least about 98% identical to the nucleic acid sequence of SEQ ID NO: 3, about 98% identical to the nucleic acid sequence of SEQ ID NO: 5, about 98% identical to the nucleic acid sequence of positions 101 through 256 of SEQ ID NO: 9, about 98% identical to the nucleic acid sequence of positions 101 through 256 of SEQ ID NO: 11, about 98% identical to the nucleic acid sequence of SEQ ID NO: 30, or identical to the nucleic acid sequence of positions 8 through 259 of SEQ ID NO: 27, and
            wherein the nucleic acid sequence encodes a peptide having an amino acid sequence identical to positions 1 through 51 of SEQ ID NO: 26, and
            a 3' termination sequence operably linked to the spinach defensin nucleic acid,
            wherein the peptide comprises a mature peptide, and
            wherein the mature peptide has antimicrobial activity in *citrus* effective against Huanglongbing *citrus* greening.

2. A method according to claim 1, wherein the first plant is orange, grapefruit or lemon.

3. A method according to claim 1, wherein the second plant is orange, grapefruit, or lemon.

4. A method according to claim 1, wherein the first plant and the second plant are both orange, grapefruit, or lemon.

5. A method of treating a *citrus* plant having and/or at risk of having a microbial infection, the method comprising:
    grafting a second plant to the *citrus* plant having and/or at risk of having a microbial infection,
        wherein the second plant comprises an expression cassette, the expression cassette comprising, in a 5' to 3' direction:
            an expression control sequence,
            a spinach defensin nucleic acid operably linked to the expression control sequence, wherein the nucleic acid sequence of the spinach defensin is about 98% identical to the nucleic acid sequence of SEQ ID NO:

3, about 98% identical to the nucleic acid sequence of SEQ ID NO: 5, about 98% identical to the nucleic acid sequence of positions 101 through 256 of SEQ ID NO: 9, about 98% identical to the nucleic acid sequence of positions 101 through 256 of SEQ ID NO: 11, about 98% identical to the nucleic acid sequence of SEQ ID NO: 30, or identical to the nucleic acid sequence of positions 8 through 259 of SEQ ID NO: 27, and wherein the nucleic acid sequence encodes a peptide having an amino acid sequence identical to positions 1 through 51 of SEQ ID NO: 26, and a 3' termination sequence operably linked to the spinach defensin nucleic acid, wherein the peptide comprises a mature peptide, and wherein the mature peptide has antimicrobial activity in *citrus* effective against Huanglongbing *citrus* greening.

6. A method according to claim 5, wherein the *citrus* plant having and/or at risk of having a microbial infection is orange, grapefruit, or lemon.

7. A method according to claim 5, wherein the second plant is orange, grapefruit, or lemon.

8. A method according to claim 5, wherein the *citrus* plant having and/or at risk of having a microbial infection and the second plant are both orange, grapefruit, or lemon.

9. A method for enhancing a *citrus* plant's innate ability to respond to contact infection with a pathogen, the method comprising:

grafting a second plant to the *citrus* plant, wherein the second plant comprises an expression cassette, the expression cassette comprising, in a 5' to 3' direction:

an expression control sequence, a spinach defensin nucleic acid operably linked to the expression control sequence, about 98% identical to the nucleic acid sequence of SEQ ID NO: 3, about 98% identical to the nucleic acid sequence of SEQ ID NO: 5, about 98% identical to the nucleic acid sequence of positions 101 through 256 of SEQ ID NO: 9, about 98% identical to the nucleic acid sequence of positions 101 through 256 of SEQ ID NO: 11, about 98% identical to the nucleic acid sequence of SEQ ID NO: 30, or identical to the nucleic acid sequence of positions 8 through 259 of SEQ ID NO: 27, and wherein the nucleic acid sequence encodes a peptide having an amino acid sequence identical to positions 1 through 51 of SEQ ID NO: 26, and a 3' termination sequence operably linked to the spinach defensin nucleic acid, wherein the peptide comprises a mature peptide, and wherein the mature peptide has antimicrobial activity in *citrus* effective against Huanglongbing *citrus* greening.

10. A method according to claim 8, wherein the *citrus* plant is orange, grapefruit, or lemon.

11. A method according to claim 8, wherein the second plant is orange, grapefruit, or lemon.

12. A method according to claim 8, wherein the *citrus* plant and the second plant are both orange, grapefruit, or lemon.

* * * * *